US007368547B2

(12) United States Patent
Lawrence et al.

(10) Patent No.: US 7,368,547 B2
(45) Date of Patent: May 6, 2008

(54) **USE OF NOVEL VIRULENCE-SPECIFIC GENES AS TARGETS FOR DIAGNOSIS AND POTENTIAL CONTROL OF VIRULENT STRAINS OF *LISTERIA MONOCYTOGENES***

(75) Inventors: Mark L. Lawrence, Starkville, MS (US); Dongyou Liu, Starkville, MS (US); A. Jerald Ainsworth, Starkville, MS (US); Frank W. Austin, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 519 days.

(21) Appl. No.: 10/767,441

(22) Filed: Jan. 30, 2004

(65) Prior Publication Data

US 2004/0267002 A1   Dec. 30, 2004

Related U.S. Application Data

(60) Provisional application No. 60/458,414, filed on Mar. 31, 2003, provisional application No. 60/447,297, filed on Feb. 14, 2003, provisional application No. 60/444,201, filed on Feb. 3, 2003.

(51) Int. Cl.
| | |
|---|---|
| *C07H 21/02* | (2006.01) |
| *C07H 21/00* | (2006.01) |
| *C07H 21/04* | (2006.01) |
| *C12P 21/04* | (2006.01) |
| *C12N 1/20* | (2006.01) |
| *C12N 15/00* | (2006.01) |
| *C12N 15/63* | (2006.01) |

(52) U.S. Cl. .................... 536/23.1; 536/23.7; 536/24.3; 536/24.32; 536/24.33; 536/25.4; 435/71.1; 435/71.2; 435/252.3; 435/320.1

(58) Field of Classification Search ............... 536/23.1, 536/23.7, 24.32, 24.33, 24.3, 25.4; 435/320.1, 435/71.2, 252.3, 71.1
See application file for complete search history.

(56) References Cited

U.S. PATENT DOCUMENTS

| | | | |
|---|---|---|---|
| 2004/0018514 A1* | 1/2004 | Kunst et al. .................... 435/6 |
| 2006/0078901 A1* | 4/2006 | Buchrieser et al. ............ 435/6 |
| 2006/0257894 A1* | 11/2006 | Doumith et al. ................ 435/6 |
| 2006/0278795 A1* | 12/2006 | Lee ............................. 248/371 |
| 2007/0190029 A1* | 8/2007 | Pardoll et al. ............. 424/93.2 |
| 2007/0190063 A1* | 8/2007 | Bahjat et al. ............. 424/155.1 |
| 2007/0207170 A1* | 9/2007 | Dubensky et al. ....... 424/234.1 |
| 2007/0207171 A1* | 9/2007 | Dubensky et al. ....... 424/234.1 |

FOREIGN PATENT DOCUMENTS

WO    WO 02/28891 A2 *  4/2002

OTHER PUBLICATIONS

Peters et al, FEMS Immunology and Medical Microbiology, 2003, 35:243-253.*
Liu et al, J. Clinical Microbiology, Jan. 2006, 44/1:214-217.*
Cossart, Int. J. Med. Microbiol., 2002, 291:401-409.*
Franciosa et al, FEMS Immunology and Medical Microbiology, 2005, 43:431-439.*
Schmid et al, Systematic and Applied Microbiology, 2005, 28:1-18.*
Tsai et al, Infection, Genetics and Evolution, 2006, 6:378-389.*
Churchill et al, J. Microbiological Methods, 2006, 64:141-170.*
Low et al, The Veterinary Journal, 1997, 153:9-29.*
Portnoy et al, Infection and Immunity, Apr. 1992, 60/4:1263-1267.*
Vazquez-Boland et al, Microbes and Infection, 2001, 3:571-584.*
Kreft et al, Int. J. Med. Microbiol., 2001, 291:145-157.*
Liu et al, J. Medical Microbiology, 2003, 52:1065-1070.*
Sabet et al, Infection and Immunity, Oct. 2005, 73/10:6912-6922.*
Aznar, et al., "On the specificity of PCR detection of *Listeria monocytogenes* in food: a comparison of published primers." System Appl. Microbiol., 25:109-119 (2002).
Bassler, et al., "Use of a fluorogenic probe in a PCR-based assay for the detection of *Listeria monocytogenes*." Applied and Environmental Microbiology, 61(10):3724-3728 (1995).
Blais, et al., "A nucleic acid sequence-based amplification system for detection of *Listeria monocytogenes* hlyA sequences." Applied and Environmental Microbiology, 63(1):310-313 (1997).
Bohne, et al., "Differential regulation of the virulence genes of *Listeria monocytogenes* by the transcriptional activator PrfA." Molecular Microbiology 20(6):1189-1198 (1996).
Bubert, et al., "Detection and differentiation of *Listeria* spp. by a single reaction based on multiplex PCR." Applied and Environmental Microbiology, 65(10):4688-4692 (1999).
Bubert, et al., "Differential expression of *Listeria monocytogenes* virulence genes in mammalian host cells." Mol Gen Genet 261:323-336 (1999).
Camilli, et al., "Dual roles of plcA in *Listeria monocytogenes* pathogenesis." Molecular Microbiology 8(1):143-157 (1993).
Carpenter, et al., "Survival of *Listeria monocytogenes* on processed poultry." Journal of Food Science 54(3):556-557 (1989).
Domann, et al., "A novel bacterial virulence gene in *Listeria monocytogenes* required for host cell microfilament interaction with homology to the proline-rich region of vinculin." The EMBO Journal 11(5):1981-1990 (1992).
Donnelly, et al., "Method for flow cytometric detection of *Listeria monocytogenes* in milk." Applied and Environmental Microbiology, 52(4):689-695 (1986).
Doyle, et al., "Survival of *Listeria monocytogenes* in milk during high-temperature, short-time pasteurization." Applied and Environmental Microbiology, 53(7):1433-1438.
Erdenlig, et al., "Production of monoclonal antibodies to *Listeria monocytogenes* and their application to determine the virulence of isolates from channel catfish." Applied and Environmental Microbiology, 65(7):2827-2832 (1999).

(Continued)

Primary Examiner—N. M. Minnifield
(74) Attorney, Agent, or Firm—DLA Piper US LLP

(57) ABSTRACT

A method for identifying virulent strains of *L. monocytogenes* that includes the use of primers or probes in a PCR assay or hybridization technique that employs primers or probes, which are specific for virulence-specific genes of *L. monocytogenes*. Also provided is a method of control of *L. monocytogenes* strains that have been identified using the method of the present invention.

13 Claims, 8 Drawing Sheets

OTHER PUBLICATIONS

Erdenlig, et al., "Pathogenicity and production of virulence factors by *Listeria monocytogenes* isolates from channel catfish." Journal of Food Protection 63(5):613-619 (2000).
Farber, et al., "Thermal resistance of *Listeria monocytogenes* in sausage meat." Acta Microbiologica Hungarica 36(2-3):273-275 (1989).
Farber, et al., "Monoclonal antibodies directed against the flagellar antigens of *Listeria* species and their potential in EIA-based methods." Journal of Food Protection 50(6):479-484(1987).
Franciosa, et al., "Characterization of *Listeria monocytogenes* strains involved in invasive and noninvasive listeriosis outbreaks by PCR-based fingerprinting techniques." Applied and Environmental Microbiology, 67(4), 1793-1799 (2001).
Freitag, et al., "Examination of *Listeria monocytogenes* intracellular gene expression by using the green fluorescent protein of *Aequorea victoria*." Infection and Immunity, 67(4):1844-1852 (1999).
Gellin, et al., "Listeriosis." JAMA 261(9):1313-1320 (1989).
Glaser, et al., "Comparative genomics of *Listeria* species." Science, 294, 849-852 (2001).
Glaser, et al., "From the pathogenic to the innocuous: comparison of the *Listeria monocytogenes* and the *Listeria innocua* genomes." GenBank Accession# NC-003210 (2001). http://www.ncbi.nlm.nih.gov, p. 1 and 2 of 1,771, printed Jul. 16, 2004.
Graham, et al., "Inter- and intraspecies comparison of the 16S-23S rRNA operon intergenic spacer regions of six *Listeria* spp." International Journal of Systematic Bacteriology, 47(3), 863-869 (1997).
Gray, et al., "*Listeria monocytogenes* and listeric infections." Bacteriological Reviews, 30(2):309-373 (1966).
Heisick, et al., "*Listeria* spp. found on fresh market produce." Applied and Environmental Microbiology, 55(8):1925-1927 (1989).
Hof, et al., "Is any strain of *Listeria monocytogenes* detected in food a health risk?" International Journal of Food Microbiology, 16:173-182 (1992).
Klein, et al., "Sensitive detection of viable *Listeria monocytogenes* by reverse transcription-PCR." Applied and Environmental Microbiology, 63(11): 4441-4448 (1997).
Kuhn, et al., "Molecular studies on the virulence of *Listeria monocytogenes*." Genetic Engineering, 17:31-51 (1995).
Lamont, et al., "*Listeria monocytogenes* and its role in human infection." Journal of Infection, 17:7-28 (1988).
Lennon, et al., "Epidemic perinatal listeriosis." Pediatric Infectious Disease, 3(1):30-34 (1984).
Liu, D., "Development of gene probes of *Dichelobacter nodosus* for differentiating strains causing virulent, intermediate or benign ovine footrot." British Veterinary Journal, 150(5):451-462 (1994).
Liu, et al., "*Dichelobacter nodosus*: differentiation of virulent and benign strains by gene probe based dot blot hybridisation." Veterinary Microbiology, 38:71-79 (1993).
Nishibori, et al., "Correlation between the presence of virulence-associated genes as determined by PCR and actual virulence to mice in various strains of *Listeria* spp." Microbiol Immunol 39(5), 343-349 (1995).
Norton, et al., "Detection of viable *Listeria monocytogenes* with a 5' nuclease PCR assay." Applied and Environmental Microbiology, 65(5):2122-2127 (1999).
Norton, et al., "Characterization and pathogenic potential of *Listeria monocytogenes* isolates from the smoked fish industry." Applied and Environmental Microbiology, 67(2):646-653 (2001).
Pine, et al., "Cytopathogenic effects in enterocytelike Caco-2 cells differentiate virulent from avirulent *Listeria* strains." Journal of Clinical Microbiology, 29(5):990-996 (1991).
Portnoy, et al., "Role of hemolysin for the intracellular growth of *Listeria monocytogenes*." J. Exp. Med., 167:1459-1471 (1988).
Portnoy, et al., "Molecular determinants of *Listeria monocytogenes* pathogenesis." Infection and Immunity, 60(4):1263-1267 (1992).
Poyart, et al., "The zinc metalloprotease of *Listeria monocytogenes* is required for maturation of phosphatidylcholine phospholipase C: direct evidence obtained by gene complementation." Infection and immunity, 61(4):1576-1580 (1993).
Roche, et al., "Assessment of the virulence of *Listeria monocytogenes*: agreement between a plaque-forming assay with HT-29 cells and infection of immunocompetent mice." International Journal of Food Microbiology, 68:33-44 (2001).
Rodler, et al., "Examination of *Listeria monocytogenes* in milk products." Acta Microbiologica Hungarica 36(2-3):259-261 (1989).
Sallen, et al., "Comparative analysis of 16S and 23S rRNA sequences of *Listeria* species." International Journal of Systematic Bacteriology, 46(3):669-674 (1996).
Schuchat, et al., "Epidemiology of human listeriosis." Clinical Microbiology Review, 4(2):169-183 (1991).
Smith, et al., "The two distinct phospholipases C of *Listeria monocytogenes* have overlapping roles in escape from a vacuole and cell-to-cell spread." Infection and Immunity, 63(11):4231-4237 (1995).
Vazquez-Boland, et al., "Nucleotide sequence of the lecithinase operon of *Listeria monocytogenes* and possible role of lecithinase in cell-to-cell spread." Infection and Immunity, 60(1):219-230 (1992).
Vazquez-Boland, et al., "*Listeria* pathogenesis and molecular virulence determinants." Clinical Microbiology Reviews, 14(3):584-640 (2001).
Wiedmann, et al., "Ribotypes and virulence gene polymorphisms suggest three distinct *Listeria monocytogenes* lineages with differences in pathogenic potential." Infection and Immunity, 65(7):2707-2716 (1997).
Winters, et al., "Rapid detection of *Listeria monocytogenes* by a PCR assay specific for an aminopeptidase." Molecular and Cellular Probes, 13:127-131 (1999).

* cited by examiner

FIGURE 1

Listeria monocytogenes virulence-specific gene sequences

SEQ ID NO: 1
lmo0833

```
tataggagac gatttaaatg
   223801 gttgcgtatg gtgagttaat tcgcgaagta cggctttcaa aaggactaac gcaaaaagaa
   223861 gtttatacag gagtaatttc aaaatcatat gcaataggtt ttgaaaaagg aaaacatgat
   223921 attacattag tactatttga agaaatttta gaacgggtca tgttaagttc agatgaattt
   223981 ttctttatga ataggggcta ttctttagcg gaggaagata atttttggta caaatttgca
   224041 aatgcagcta atcaaaaaag tttggcagaa ttacaagaat tataccaaga agtattgcag
   224101 caaaatggcg atagagcgaa tctaaggaaa gcaattgtcc actcgagaat tgaaattaat
   224161 gaacaatttc ttttgaataa tcgatttgac gttagtatcg tttctgagga agataaagca
   224221 gttatccaaa cgtatttgtg gaaagttcaa tcatggacac tagaagaaat tcggattttc
   224281 gctaattcag tggactattt tgaagaagat gtacaaattt atttttttca attggtcttg
   224341 aagtcactcg aaaaatataa gcattacgat cgtggtaaaa aagtattttc cacgctactc
   224401 accaacataa tagaagaact aatcacccgt gatcaattag aatatgccgc gcaattatta
   224461 gaaatactgc acgaactttc ttctacgcat gactgtgctt tttaccggat tatgcataat
   224521 tactatcaag gcttaatatg gatgaaaaat gacgaggtcg aacaaggctt aaaagagtct
   224581 aaaagtgcaa tccgaatttt agatgcactt gattacaaat ccctcgcgct actttataat
   224641 acattacttc aacagttttt agaaaaagag aatatacaaa tagtttaaag taaatcagat
  224701 acctttata aggtatctgt ttttttggtc
```

SEQ ID NO: 2
lmo1188

```
tggagataaa aaaggatgct
    53641 tactaaaata gctacttatg gttgttgtgc aacaagggat ttgttcaata aagcatttgt
    53701 tagtgattgg aaaaatcatt ttcaattagt gtcatatcaa cagcattgca gtattgtttc
    53761 actaatgtca aagccaattg atatcgaact aggagaagaa ctgctgggag agttaagtaa
    53821 ctttgaaaaa agtgtattta aacaagacgt attaaaatct tttttagaaa ctttaaaaac
    53881 aactcaacca gaatatttag tgttagattt tcatgtggat acattcaatg gttttattga
    53941 actcactgat gggggggatta tcactaatcg aatcgtccgc tataagaaat tggatatttt
    54001 taataaaatg gaagcaagga aagtttttttc gccgttagaa aatacgactg agtttagaaa
    54061 acgttggata cagagtttta accgttttat gcaatttatg aaagaaaatt gccctaatac
    54121 ccaaattatc attaataggt tagaggttgc acgaatgtat tattctttag ataaccaaat
    54181 ggaaagcatg atagaacgta gaaaaacaaa agatcaccat actgctgaga cattagctaa
    54241 aattgatgag tgcatagatt actttgagcg ttatgctatg aataattttg atttacagtc
    54301 attggacttt aattccgaag aatactttgg tgcagaaaat aatccatggg gaacctgtta
    54361 tatgcattac aatccctatt attataaaaa aaagtttaaa gatttatgga atatagttga
    54421 aaatcatttt catgcaccaa caaaattagc tagttttgca cctggaggcc ttgcgaaaca
    54481 aattccatta ggtgtgacca aattatctga tatggatgaa gtaggagtat attatttaac
    54541 aaatgctact tacttacaaa tggaggatcg accgacaaca gataatgcag gttatttttt
    54601 cattgtttat ccgcgaaatg ggaaaaatgg gtatatgcaa gagctgagaa aatcaacagc
    54661 agctttttcc attcaaattt ttgtccgaat tactgatgga aaagagagtt ctaaatggaa
    54721 catggtaaat agtggctttc gaacacttac aatacctgat gtgacttcta tttctgaaat
    54781 tacagaggct ggagaatatt atattactgc agaacaggtt aacaaacttc aggatcatcc
    54841 tacaaagaaa aatggttggt ttctaaccgt ttctaagaaa aatcatgata gcctaaaaca
    54901 attgttaaca aaaaatactc aaaatgacaa tgcctttgaa gaatatgttc gacttgtaaa
    54961 cgtggaaaaa agaacaaact taaaatggcg taaatatcat tttgatgaag caaacttttc
    55021 gattatagtt gctatacgta actttaaaaa caaagtggta cgaagattaa aattaacaaa
  55081 agcataaaca
```

FIGURE 1 – (CONT)

SEQ ID NO: 3
lmo0834 aggagagatt
```
     224821 tttatattaa atcaaaaata tcaattacta cttcataatg aatatgacac aaaaagtggt
     224881 gatttagtca aaaagaaat  agttgcaact aaaaaaacta aaatctctt  ggaagatcta
     224941 acttcgcatt tgttatgtgt tacaaatcaa atagagtatg gaaatttat  cacttggtat
     225001 gaaatggaaa ttaaaaaagt tctacaagtt catcccaatc agcactttat tattaaaatt
     225061 tcctttcaac aattatattt tcgggaaaca atgctgttgc ttgagaattt acagaaagat
     225121 agccggcgac taacgattga gctagttgga gatagtcaga ttagcccta  ttcaaaggaa
     225181 cattttccg  cagaggacag tgatgctttt ttgaaaggga agttaaaaat gttgaaaaag
     225241 tggcattatt ttatttcaaa gcatattgaa agtggtgcca tcgaacaaac actgattttt
     225301 acgccctata ttgatgaatt gaaatatagt ttaacgcaaa agtcgaagct cttacacaat
     225361 attactgaat taaagttttt tctatcattt tggaaaaatt gggctgagct tcgatttgtt
     225421 gatttttag  ttttagtaga tgaaaaaac  gaatttgtat cgcatgtgct tttaccagat
     225481 gaattaaatg tacgttgcaa aatgtatgag aactttggag gaatggtcag tgagtaaaaa
```

SEQ ID NO: 4
lmo1116

```
262981 aaaaactgtt ctaaaaagga gggggaacga tgaaaacgaa gatgccggaa atgctttctt
   263041 tcatttcaga agaagctgtt agtagaaaaa tgacaagtga ggaaattgct gctcactttg
   263101 gttatgataa acatcacttt agtcgaaaat ttaaagaaat taatggattc agtgtggttg
   263161 aatttctttc tagtttaaaa gtggaaaagg cgattattga acttgatgaa gaagtacgca
   263221 tactcgactt acaagaacat tcaggttttg aaagtagtgg tagtttcaca aatacgttta
   263281 aaaatatac  aggtagttct cctagaaaat acaaaaccga aatgaatgat attttttatg
   263341 atatgaaacg ttttgaaaat gataataagg ataagtcaat agcgcatttt caagaaaata
   263401 atgattcttt ttgcaatgta actattgatg tacctgatga atttgagaag ggtatcatat
   263461 ttattggact tttccgtact cttataccga atcatatgcc tatatcggga ttagctacta
   263521 aaaatttaat aggaaatcaa ttgaaaaata ttccaagcgg agactattat ttattagctt
   263581 gtgcgataag ccagtctaat aacattctat cttattttaa cttaagtaat agtttgagag
   263641 ggaaagaaga tgaaaagcta tctttttccta aatgttctgg caatcattac gcgattaagc
   263701 tgagaaaacc aataccagaa gatccaccaa tattagctaa tgtgggaaaa attttaatct
263761 cctgtttgaa gaacacaatc tagaacaatt
```

SEQ ID NO: 5
lmo2672

```
25921 aaacaaattc attaatcatt ttaagcacct ccatatcatt agtttaacaa agcatttacg
    25981 tttttcattg tatatttgcg acattttgca gaaaaatttg cttcatttct tctgggggtat
    26041 gattactata tcgtttaaat tgtttaatta agtgagcctg gtccgtaaac ccatgaagat
    26101 aagcaagttc agcgcccggc acacttggat tctcatataa tgcctgtaat acttttggga
    26161 aacgaataag ttttgctgtc tgtttaggtg caagtcccat gtgttttga  aacagccgtt
    26221 ctaactgccg aacagataca gctcctaaca caattgatt  ggggttttgt agtaacttat
    26281 caatactgtt taaaaaatca ggatggactt gcttgccaag catcattaat tttcgcagta
    26341 aaaattcttc taataaagct attctttcac tgttcgtcgt catttcagca aacctctctt
    26401 gaaaaacga  aacaaatcca gcaaacatct cttccggctc ttttacccga ttcatgctac
    26461 cagtcaagtc ctgttcgaca aataaaaata cgaccacgc  ataaaatcgc acggcaaaaa
    26521 gctcggtatt actttcatcg tcagactcaa acgatgcatc actaacgcca acaaatatag
    26581 catccgtcac tagccctgtt ttactatcaa ttgtaaaaat aatatccgca cataaatcag
    26641 gaaccactaa attatttccc gggaaattct tatcatctgc ctcccaaaaa cagcgaatat
    26701 agcctgtaag agctgcactc ggtagatatt ctttatagcc agcacgcttt ggtgtagcta
    26761 caatgggata aaacgtttct agcttagcca taaagagacc ccctttttcct catagtacca
    26821 caaatttc   tctttaatca tgcttctttc tttatttat  gggtattaag taaataaggg
 26881
```

FIGURE 1 – (CONT)

SEQ ID NO: 6
lmo1134 ggagtacacc cgatagcaag gaggaactag atgtatatta aagattttgc
    8041 cactaaaacg gggctttcga ttgatacgct tcgatattat gaggaagaaa aattattaat
    8101 acctgctaga aatgaaaaaa attatcgtgt ttatacggaa gaagattact gctgggtaca
    8161 gcttttactt aaaatgaagc aaacagagat gacaataaca aacattaaaa attttgctac
    8221 attacaaaag caaggagata aaacactccc aaatcggata caaattttag ataatcatat
    8281 ggaaaacttg tatgaacaac agaaagattt agcagaaacg atttcttttg tggctaaaaa
    8341 agtggatggg tatcgagaga agttaaaaa acaacaggaa

SEQ ID NO: 7
lmo0333 aagtcttgaa aaagaaattt agtatagtta
     961 ttatcagtgt attgttactt ggttatttag cgccttttga tactttgtta gtaggtgcag
   1021 atgaaacaac ggtttctgaa gatacagcag ttaaaacggc agaagcagat agtgctactg
   1081 aaggcataga aagcgaaaca ggttcagatg atgaaacggc agaagagcca aagaagcaa
   1141 aagaggcaga agcaagcaaa gaaacgacag aaaaagagga aaaagcgaaa acggaagaac
   1201 cggcttctaa tattaaaacg gagattaata cagataaaag ccagctgaaa caaactagct
   1261 taaaagcagc ggtgccagca ggaagtacat ataattcttt gtttccagac gacaatcttg
   1321 ctaaaaaatt agctgtgatt atcacaggaa atgcggctgc aacaggtaat gaatcagtgg
   1381 atagtgcagc tcttttagca ataagccaac ttgatttgag tggggaaacg ggcaatgacc
   1441 caacggatat ttccaatatt gaaggattac aatatttaga gaatttaaca agcctgaatt
   1501 taagtgagaa taatatatcc gacttggctc cacttaaaga tttggtaaac ctggtttcac
   1561 ttaaccttc ttccaatcga acattagtaa atctttcagg ggtggaggat ttagttaatt
   1621 tgcaagaact taatgtctct gcaaataagg cgttagaaga tatttcacaa gttgcatcgt
   1681 tgccagtgtt aaaagaaatt agcgcgcaag gctgtaatat taaaaccttg gaattaaaga
   1741 atccggctgg tgctgttttg ccagaactag aaacatttta tttgcaagaa aatgatttaa
   1801 ccaacttaac ttcattagcg aaacttccaa aattaaaaaa tctctatatt aaagggaatg
   1861 cttctttaaa aagtttagag acattgaacg gggcgacgaa gctccaattg attgatgcga
   1921 gtaactgtac cgatttagaa acgcttggag atattagcgg gctttcggaa ctcgaaatga
   1981 ttcaattaag tggttgtagt aaactgaaag aaatcacaag cttgaagaac ttgcctaatc
   2041 tggtgaatat tacggcggat agctgtgcaa ttgaagattt aggaacactg aataatttac
   2101 caaaattaca gacattagtt ctttcagaca atgaaaattt aaccaatatt actgcaatta
   2161 ccgatttacc acaattaaaa acattaactt ggatggctg tggaattaca tctattggaa
   2221 cgcttgataa ccttcctaaa ttagaaaaat tagatcttaa ggaaaatcaa ataactagta
   2281 taagtgaaat aaccgactta ccgcgattaa gctatttaga tgtaagtgta aataatctta
   2341 caaccatagg ggacttgaaa aaattacctc tattagaatg gctgaatgtt agttcgaata
   2401 gattatcaga tgtgagtaca ctaacaaatt tcccgagttt aaattatatt aatatatcaa
   2461 ataatgtcat tagaacagtc ggtaaaatga ctgaattacc ttcgcttaag gaattttacg
   2521 ctcaaaataa cagtatatca gatatttcga tgattcacga tatgccgaat ttaagaaaag
   2581 tggatgcgag taacaaccta attacaaata taggtaccct tgataattta ccaaaattgc
   2641 aaagtctaga tgtgcattca aatagaatta caagtacatc agttatacat gatttaccaa
   2701 gcttggagac gtttaatgcg caaactaatt tgattaccaa tattggtacg atggataatt
   2761 taccagattt aacctacgta aacttatctt tcaacagaat accgtcgctt gctccaattg
   2821 gtgacctacc caatttagaa acattaatag tatcagataa taattcttat taagaagcc
   2881 taggaacgat ggacggtgtt cctaaactga gaattttaga tttacaaaac aattaccta
   2941 attacactgg aacagaagga aacctaagtt cattaagtga tttaacaaat ctaacggaat
   3001 taaatttgcg aaataatgtt tatattgatg atataagtgg actttccacg ctatcaagac
   3061 tgatctactt gaatttagat tccaataaaa ttgaagatat ttctgcattg tctaatttaa
   3121 cgaatcttca agagttaaca cttgaaaaca caagattga aacatttca gcacttagtg
   3181 atttggaaaa tttaaacaag ctagttgtat caaaaaataa aattattgat attagtcctg
   3241 tcgctaatat ggttaatcga gggcaattg taactgcgag taatcaaaca tatacattgc
   3301 caactgtatt atcatatcaa agctcgttta ccatagataa tccggttatt tggtatgacg
   3361 gcacactact agcgccatca tccataggaa actctggtaa ttacaaggac gggaaaataa
   3421 cttggactaa tatgaccgct acgtctagtt ccactttatt taactttaat aggttaaaag
   3481 acggtttaac cttctcagga acagtcaccc aacctataa atctgcagcc aaagtaactg
   3541 cagatgcaga gcaaacttat acaattggtg atactatttc agaggagcag tttttaaaag

FIGURE 1 – (CONT)

SEQ ID NO: 7 CONTINUED

```
3601 atgttaatgc aaaatcatca gacggggcac ctgttacaag tgattttgct acagtggtgg
3661 atttaaacac ttttggcgaa tatgaagtta ctttaacttc cgaaaaagat ggaatccaag
3721 gggatagttg caaagtaatt gtcaaagttc ttcacggagc gcctgtcatt tcggcagacc
3781 aaacaattag ttatgataaa catgcaacta ttacagagaa acaatttta gaagatattc
3841 atgccagcac agacttggat acagctatta caaccaattt tagtacagca gttaacttga
3901 ataaaggcgg agattataca gttgcactaa actctgaaaa tgaggacggc gtgaaagctg
3961 aaacggttta tgtcactgtt actgtaaata aagacccagc gccgattata agtgctaaga
4021 cagaaatcac gtatgataaa ttctcgaaaa aaaccgaagc ggcgttctta gatgatatag
4081 acgcagatac aaatgatggc tctatagtaa cttctaattt tgctacagca gttaatttag
4141 ataaagctgg tgattatact gttacactga attctattaa tagtgatggt gtagcgggca
4201 cgccaacagc gattattgtg catgtggaga aagagaaaat agcaacaatt agcacaaata
4261 cggcacaaca atatgaaaaa tatgcgaaga ttaatgaaac gcaatttcta aaagatgttc
4321 atgctagtat taacgcgagc ccaacaaccg cagttttgga aagtgatttt gaaacagtag
4381 ttaaactaga cgtcccagga acgtacacag taacgattac tgctacaaat gaagatggcg
4441 gagtatcggc acctaaagaa gtttctgtca tagtaaggaa aattccagca ccagagatca
4501 ctgcagataa ggaaataact tatccgaaat ttgatgaagt aagtgaagca gaattttaa
4561 atgatattca tgcaactatt agtgacaaaa atgtagcgat tacaagtaac ttcagcacag
4621 atgtgaattt aaataaagct ggcgattaca cagtaacatt aaatgctacg aatgaagacg
4681 gcgtaaaggc tacaccggtt gaagtaattg tacatgttca acaaggagaa cgccctgtta
4741 taacagccga tgcaactatt tcctatgaca agttcgctaa cataacggaa gcgaagttct
4801 tagaagatat tcatgcaaca agtagtgatg gtcaaagctc tactgtaatc acctctaatt
4861 tccagaccgc gacaaacttc aaaacagcca tgagctacac agttacgctt aatgctgtaa
4921 atgaagacgg cattagcgca gaaccagtag cagtgaccgt tacaataaat aaagaaccag
4981 ccgcggcgtt aaaagctgat gcagaagtaa gctatgcgaa aaatgaagct gtaaccgaat
5041 ccgatttctt caaagatgtt catttagaag aacggaagc gccaagtaca gccaaagcaa
5101 caagtaattt tgattccgta gtagatagaa gtaaaacagg agattatact gttacgataa
5161 atgctacaaa cgaagatggg gctgtttcta caccaattga gtaattgtt catattgaag
5221 cagaaagtgc accagtaatt acagcgaatg cagaagtaaa atataacaaa catgaacaaa
5281 cagacgaaag aagatttta tatgatagtg aagcaaaaat cgatgaagct aatgtggaaa
5341 ttaaaaccga tttttgcagaa aaagtagata ttaataaagt tggaacttat actgtcacac
```

SEQ ID NO: 8
lmo2470

```
gaaaggactg aatacattga gaaaagtttt
    149281 aatgttttta agcacagctt tattattagc cattctgtca ctaagcttta ctggtttaga
    149341 tctgaaggca aaagctgctt ctgatttata tccactacct gctccaatta ttgatgtttt
    149401 cccagatgat ggattagcca aagatatggc taaaaactta aacaaagact ctgtgaatga
    149461 tgttattgac caagatgact tggatgcgat aactggtttg ggatttgaaa caagtacgat
    149521 tacgaatgat tccatgcaat tactagaacg tgccatgttt aacaatgtca cagatgtaag
    149581 tattatgaa tttggggcta aactaacgga gttccctgat attacaacca tcccacattt
    149641 aaaaacgtta ttttttgctg atccacctgg aagattaact agaaacttgt cccttccaaa
    149701 ctaccaaaat tatcctgaaa tggataccat tacaatgagc ggaaataatt taatcggttc
    149761 tatccctgat ttcactggaa tgcctgcttt aaaacagctg tatatgtctg aaatgttaat
    149821 tacaagcgat gaacttccta attttaataa tattccttta cttattacgt tggatctaag
    149881 ttctaaccaa ttgacaacta ttcctgattt tcaaaatata ccaaatctca cattttaga
    149941 tttaaatgca aatttattaa ccaatacacc tgattttcaa aattaccta aattaactga
    150001 tttaaattta agacataaca atttaactgg tacgatggtt aactacacca acttacctag
    150061 tttagaatcc ttaaacttag attacaattt tttaactgaa ctaccgtcta atgtattaga
    150121 taccatctat gttcaaagtc aaaacggaga gcttcctgat caaactatta atcaggcga
    150181 tacctgtact attgatttac ctatttattt ccaaatggaa gaaactaata tgttagtcag
    150241 cccagaagtt acgggagaat atatcgggat tagtgtaatc cagcttccga cgacggttaa
    150301 tgaggaaggc aacaccataa cagtggatac atccgctcta agtcctggtg agtataaatt
    150361 agatgtctcg tataatcaca attatgctac tggaggcgta tgctcttatg attggaatgt
    150421 aactattaat taatttctac
```

FIGURE 1 – (CONT)

SEQ ID NO: 9
lmo2821

```
188101 taaaacggcg tataataaat gattatagag aacgaataag gagtgcgcca aattgaaaac
188161 tactaaaata gtaattgcct cattagttag tttaaccatg gtttcaaacc cgcttttaac
188221 attcgcagca acgaatgatg ttattgataa tacgacagaa atcactactg ataaagaaac
188281 aagctcaact caaccaacta taaaaaacac actcaaagcc ggtcaaacac aaagttttaa
188341 cgactggttt cctgatgaca attttgcttc agaggtagca gcagcatttg aaatgcaagc
188401 aactgacact atcagcgaag aacaactagc tactctaaca agtctagatt gccataattc
188461 atccataacc gatatgactg gtattgaaaa attaactggt ttaacaaaat taatttgcac
188521 aagtaacaac attaccaccc ttgatcttag ccaaaacact aatttaactt atctggcatg
188581 tgattcaaat aaacttacaa accttgacgt aacccgctt acaaaattaa cctacttaaa
188641 ttgcgacacg aacaaactca caaagttaga tgtaagtcaa aatccactgt taacttattt
188701 aaactgcgcg cgcaacacct taaccgaaat agatgtcagc cacaatacac aattaaccga
188761 gctagactgc catttaaata aaaaaatcac caaattagat gtgacaccac aaactcaatt
188821 aacaacctta gactgtagct ttaataaaat aactgaatta gatgtaagtc aaaataaact
188881 actgaaccgt ctaaactgcg cactaataa tataactaaa ctggacctca accaaaatat
188941 tcagctaact ttcctagatt gctccagtaa caaattaacc gaaatagatg taaccccgct
189001 tacacagtta acatattttg attgtagcgt aaatccttta actgaattag atgtatctac
189061 gctttcaaaa ttaactacac tacattgtat acaaacagat ttattagaaa tagacctaac
189121 acacaacaca caattaatat attttcaagc tgaaggatgt agaaaaataa aagagcttga
189181 tgtcacgcat aatacacaat tatatttatt agactgccaa gccgctggta taacagaatt
189241 ggatctttca caaaacccta aattagtcta tttgtattta ataatactg aactaacgga
189301 attagacgtt tcccataaca caaagctgaa aagtttgtct tgcgtaaatg cgcacatcca
189361 agacttctct tctgtaggta aaattcctgc ccttaacaat aattttgagg ctgaagggca
189421 aacaatcacg atgcctaaag aaactttaac aaacaacagc ttgaccattg cagttagccc
189481 tgatttatta gatcagtttg gaaatccgat gaatattgaa ccgggagacg gcggtgtgta
189541 cgaccaagca acaaatacaa taactggga aaatctcagc acagacaatc cagccgtaac
189601 ctatactttc acttccgaaa acggagctat agtaggaacc gtaacaactc catttgaagc
189661 acctcaaccc atcaaaggag aagacgtcac agtacattac cttgatgaca aaggagaaaa
189721 attggcggat gatgaagttc taagcggtaa tttggacgat ccttatactt ctagcgcaaa
189781 agacatccca gattatacat taacgactac tccagataac gcaaccggaa cattcaccac
189841 tactagccag tccgtaacgt acgtttacac taaaaacatc gtagccgcag agcctgtaac
189901 cgttaattac gtggacgata ctggaaaaac gctctctcca tccgaaatat taaacggaaa
189961 tgttggcgac acttataacg ccactgccaa acaaatcgac ggctacacat tatccgcga
190021 accaaccaat gcaactggac aattcacaag cagcgcgcaa accgtcaact atatttacac
190081 aaaaaatcca gcccctgaaa aaggagttgt agaaattcac tatgttgacg aagataataa
190141 acaacttaac tccaccacag aaatttctgg aacaatagga gataactaca cgactgagcc
190201 aaaaactatc gaaggctata cgttaacaac tacaccgggt aatgcaaccg gcactttcac
190261 cacaggcagc caaaccgtga catatgtgta tactaaaaac atcgaagcag cagagccgat
190321 aacagtgaat tacgtggatg ctaatggcaa aacactcgct ccatccgaaa cattaaacgg
190381 aaacgttggc gacacatata agcaactgc caaacaaatc gacggctaca cattatccgc
190441 cgaaccaacc aatgcgactg gacaattcac aagtagcgca caaactgtca actacattta
190501 tacgaaaaac acaaacacag atcaacctttt accaactaaa aaacctacga acaccacacc
190561 aaccaagcca tctaatttaa agacaaccga agtgaaaaaa gcttcagata ccctaccaaa
190621 aacaggcgat tccgcaccat ggaaatcagc tctacttggg gtattcctat catccacagc
190681 tctagttatc tggaaaaaga aaaatagta aaaagccgg acaggattaa tttcccgacc
190741
```

FIGURE 2

Listeria species-specific gene sequences

SEQ ID NO: 28
lmo0733

```
123781 aaggcggtt atctctaatg ttaaacgaaa atattaaagc aatcagaaaa tcaaaaggac
  123841 tttcgcaaga agaaattgcc atcaaactga atgtggtgcg acaaacaatc tctaaatggg
  123901 agcaaggact gtcagttcct gattccgata tgttaatctc catatcggaa gtgcttgaaa
  123961 caccagtaag cactttgctt ggagaaactg ttatggtttc aaaggttgat gatgtaaaag
  124021 caatttccga aaaactggag attataaact tacagtttgc tcaaagaaag accgccagac
  124081 gaaaaatgct ttattggcta tttgtctcgt tgtgtgccgt tatagcaata atttctgcgg
  124141 tctttataat actaaatagt ccttacttag gttgggatta tagtgatcct gaaactagcg
  124201 ttatcggagt agcttttcat acatttgaat ggttgtttgt cagattagca ccgattatcc
  124261 ttataggagg agtcgttgga attttctaa cgcggaagaa cgtataaaat cgtactatgt
  124321
```

SEQ ID NO: 29
lin0464

```
28681 aaagcattac aagatttttct taaataaata aagcaaaaca cggaaatcca ttcttcggat
   28741 ttccgtgttt ttttagatga aaaaaagcat taactttcgt aaattgagac tatatcataa
   28801 attctacgct tcatttttc acgaacatgt aatggctcta aacattcgca tttatcgcca
   28861 aaactcaaga gaatatcata gtgatactcg ttttctataa aaggaaaact gacaatgtaa
   28921 tgctcctcac catcgggata aaaattttca taagagcaat aatcaagcac tctatcgata
   28981 atggattgat gaatacgaat tttaatttct atctgcataa ttgctacaat atcttccatt
   29041 tctaactgtg gcttttgaaa atctcgcagt gtaaaagtgt cctcaagtat ttgcagacca
   29101 gacatacgag ataacctgaa taaacgaaaa tcattcctat tttggcaata cccatacaaa
   29161 taccagtggc tgcttttcat tacaagctga tatggttcaa ctattcttac ggtcttattt
   29221 cctggtgag ctatatattc aaaggttagt aacttgtttt cctgcaaagc cactttgata
   29281 atttctacat gtggttgtat gttgttattt cccgtccact ggcttaaatc tatataaatt
   29341 tggttcgctt ttagctcgat ttcttttgct ctatcagctg ggataaaact ttttattttt
   29401 gcaagagcat ttatcagttc atctccgcgt accatgttag aaagacttga aaggcccata
   29461 agaatagcgg aaaggtctgc tgttgaaaaa accttgctat ccatcttgta gtcaggcata
   29521 atttcaaacc cgccacctac gcccggtgtt gaacgaatag gtacaccagc caagtcaatc
   29581 gcgtctatgt cacgataaat tgtacgaagc gaaacttcaa atctatcagc taactcttgt
   29641 gcgctaatac gttctttatc aaggagaatt aaaacaatgc tcataagcct atcaactttc
   29701 ataatagc cacctttcaa aattactata tattgttgcc ataatggtgt caacaatcgg
   29761
```

SEQ ID NO: 30
Lgr20-246

```
GATCTGCATTGTAAACGCCATCCACATTGTTCTTCGCCATTAAAATCACGTCTGCTTCAATTTCTGCTGCCCGAAGCAGC
TGCAGTTGTATCTGTCGAGAAATATGGATTTCCCGTACCACCAGCGAAGATTACGACACGTCCTTTTTCCAAGTGTCTGA
TTGCTTTCCGGCGAATATAAGGTTCAGCGATTTGGCGCATATCGATAGAAGTTTGTACACGTGTTGCTACCCCAATATTT
TCCAAGGAATCTTGAAGAGATAAGGAATTCATGACCGTTGCAAGCATTCCCATATAATCTGCTGCTGCACGATCAAGGTC
AATCTTACCGGTCAGTTCTTAGGTCTTAAATATGTGCTACCTATTTTAACGAAACAAGGAAATGGAAGCGTTATCAACAC
GGCTTCTGTGGCCGGACTTGATGGCAGTTCCTTTTTAGCGCCATATGTGGCTTCAAAACACGGCGTCAGTGGTCTGACAA
AAGTCCGCAGCACTAGAAGTAGCGGATAAAGGTGTTCGGGTCAACTCCGTCCATCCATCACCAGTCAATACCCGGATGAT
GCGATCGATCGAAAAGAATCTCAACCCAGACGATGCGGAAAAAGCAAAAGAAGAATTTACAAAAGATATTCCAGTCGGAA
GATATGCAGAAGCCAGCGATGTCGCGAAACTTGTCTTATTCCTAGCCTCGGACGATAGCAAATTTATCACTGGTGCGCAA
TACGGGTAGATGGCGGTATGGGGGCTACACAATAAAATTAAAAATAAAGATC
```

FIGURE 2 – (CONT)

SEQ ID NO: 31
Liv22-228

GATCTTGTAGCCGATATAATAATCTCGTAATTTGTTGTTCATTAAGCATATTTATAGAACCTCCCATAATGAATGCGCTG
GCATACAGATTATTATAGCATGGCTTCATTTGTTTATCACGAATTCCTTATTCACTTGAGCTATTTATTCTAGTCTTTTT
TTAGAACATTTTTACTTTCTATAGAGAAAATTACTACTTCAAGGCTTATTACTAAGCAATAATTAATTTACTAAAAATGG
CTTTATACCAATATTCACCTGTTTTTCCGTTTTTTAAAAACAACTTTCACTAAAAACAACTTCACAATTTTTACACATTT
AACCAACTAAGTAAAAATCGCTATATATCAGTCATTTAACCAATTTTTAATTTTTCGTTATACAATTGTAATAGATTTTT
TTTCTTGTTTTTTGATATTATAATTACAAATAGATAAAAAAGGAGTGCTTAGAACTGTGGATAAAAAGTTTATGAAATCA
GGGATTATTATACTCATTGTGGCATTTATTGTAGTTTCAATGAATGTTGGAGCAGAAACGGGTGATAATCAGGTTTCTCA
AGTTGAGTTAAGTTCGCAGCAACAAGCATTTATTAATGAAATTTTACCCGCTGCTCAAGATGGTCTACGTGACGGAAAGC
TTTTAGCCAGTGTAACACTCGCTCAAGCTATATTGGAATCTAATTGGGGTGAAAGTGGTTTAAGCAAAAACTCGAATAAT
TTATTTGGTATTAAAGGTTCGTATAATGGGAAATCAGTTTCGATGCGTACGATGGAAGCAACTGGGGCAACAACTGCGAA
TTTCCGTGTTTATCCTAGCTGGCAAGAATCCATTAAAGACCATACTGATTTAATTACACACAACGCACGCTATAAAGGCG
CAGTCGGCGAAACAGATTACCGCAAAGCTATACAAGCAATTAAAGATGGTGGTTATGCGACTGATCATGGTGCAGAAACA
GTAGAAGTTAGACGCAAAAATGGTAAGAACGAAACGGCAACCATTAATTTGAAAGCCTTTCATAGTGGTAATAATGTTGT
TATCGAAATTGTAGATGATGGTGCTGGTATTAACAAGCGAAAAGTTTTAGAGAAAGCGATTACGAAAAACGTAGTAACGA
GAGCAGAATCTACCAAAATGACGGATAGCGAAATTTTTGATTTGCTGTTTGACTCAGGATTTAGTACCGCTGATCTAAAG
CTTTTCGGCTCCCTAAAAACTATCCGTGCGGAAAAAGACTATAAAAAAGGATTACAAGTGCTTGATAAAAACTTTTACGG
CACCATTTCCGACTTTGATTTAGAATAGAAGTGGCCGATTATGTCAAAGGTAAAGAAATTTTCACTAAATTATTAAAAGA
TTATCAAATAACAGATC

SEQ ID NO: 32
Lse24-315

GATCATTTATCGTATCAACATCCCGTTAGATTTTCATTTCCGGAAAGGATTAATGTTTCGTAATTTCGGTAGATTTTCTA
ATGTCCCCAAATCTTCTATTATCGCAATTATTGCAGTAATATTAGTTAAATTAGGTAGATTTTTTAAATCTGTAATTTCT
TTTAACTTACTACAACCACTTAGTTGAATCATTTCAAGGGTATGTAATCCCACTAATGTCTCCAACTGTCTCCATATCCG
TACAGTTACTCGCATCAATTAATTGGATTGAGGTAGAACCATTTAATGTTTCTAAACTTTCCAAAGAAGAATTTCCTTTG
ATATAAAGATTTTTCAATTTTGGTAATGTTGCTAATGCAGTTAAATCTTGCAAGTCATTCTCTTGTAAATAAAATGTCTC
TAGTTCAGGCAAAGCATCCTCCCGCAGGATTTTTCAAGTTCTAATGTTTGAATGTTTACAACCCTTGCGCACTGATTTCT
TTCAAGGCTGGTAACGGCTGCTACTGGTGAAATATCAGCTAAAGATTCTACCAAGTTGATACATTTAAAATCCTGTAAAC
TGGGGTAAACCTTCCCACACCCGTTTAAAGTCTTCTAAAATTTTGGTCTGGAAGAAGAGATTTATTAGCCACCTTATTTT
CCGTTAAACCAGTCAAGTCGGTGAGACATCAGTTAGGGTGAATTTCTCACTAAAATTTAACCTCCGTTTACCGTATTCTA
AAATACTAGAAACCCCCTTAATTACTCCCCAAACTCAAATGTCTTTGCACCAAGCCCGTTTCCCGCTAAATTAGTGGGGA
GGAAAAAGTCCCGCGATTTTGGTAATTTATCACAATGGGAGGGCTTCCCAGGAGCAAAAGCAATTTTTTGCCAAGATTT
TCATCTGTAACAAAGAATTATATGTACTCCCAGCAAGAACATCTGTTTTTAATTTAGATTGCTTGAAGTTGGTTTTCTG
TTTTTGGTTCTAATTTAGGAGTGACGGCTTACTTCTTTCGGATCTGTAGGTTTTTCCGCCTCTTGTTCTAATGGTTCTTC
TTTAACTTCTGTAATCTGAATTAGTTTCAATAACCGGTGTTTTTTCTTCAGTTATTTCTGATTTTGTCGTTAAATCTTCA
GGAACAGTTGTTTCTTCCGCGACGGCTAAAGTACTAAATGGAGCCAAATACCCCAACAAAAGAGCACTAACAATTACCAT
ACTAAGTTTTTCTTCAAGACTTTCCCTCATTTCGTTCAAATTAATTTAACATTTTTTGGTGCTCCATTTATTATACATG
GCTTGAATACGCCATTTGTCTTTTTAAAATACTTATCAAAACAGAAATATGTAGATTTTATGTCGCCAGAAAAACTAGTT
TTTTTAAAACGAGCTAGAATGTTGCTCTAATGCTATTTTCACTCAAAAAAAACAAGCCAGATAATTTCGGCTTGTTTCGA
TGTTTATATTATTCATTTTTATTTTTCGATAACTACTGGATTTTGTACATGTACGACTTCAAAGCGAGCAATTTCATTTC
CGACAATTCCTTTACGA

FIGURE 2 – (CONT)

SEQ ID NO: 33
1we7-571

CATTGGTGTCCTTTTAGCTGTGTGGTTAATGTGTGTGCTCGAGAAAAACTTGCGTAAAATAATTCCGAATGCGATAGATA
TCATTTTCACTCCCACATTGGTGCTACTCATTATTGGTGTAGTAACTATTTTCTTAATCATGCCATTCGCCGGACTTGTT
TCTGATGGATTAGTGAACGGAATCAACTGGGTTATCGAAGTTGGCGGTGTTTTTGCCGGATTTGTTCTTGGTACATTATT
CTTACCAATGGTCATGTTTGGTTTACATCAAGTTTTAACACCAATTCATGTAGAAATGATTGCCCAAAGTGGTTATACAA
TATTATTACCGATTTTAGCAATGGCAGGTGGTGGACAAGTCGGTGCATCCATCGCTCTTTGGATTCGTTGTCGTAAAAAT
AAACCACTTGTTAACATGATTAAAGGTGGCCTTCCAGTAGGTATTTTAGGAATTGGCGAGCCATTAATTTATGGAGTTAC
CATTCCACTTGGTAGACCCTTTCTAACTGCTTGTCTTGGTGGTGGTATTGGGGGCGCAGTGATTGGATTCTTCGGAAACA
TTGGTTCGATTGCCATTGGACCTTCTGGGGTAGCGCTTATTCCATTAATNCGCTAACAATGAATGGTTGGGATATATCAT
TGGTCTAGTAGCTGCATATCTAGGCGGATTTATCTTAACGTATTCTTTGTACGCCAAAAGATGCGATGCAAATGTGGAAT
ATAAACTAAGTTGACTAATCAAAGCCATTAAATGATTTATTATTTAATGCCCTTTACTATTTACAATAAGCAATTTAAAT
GTAAAATCAAAGAAAGAGTTTTGAC

SEQUENCE LISTING

<160> NUMBER OF SEQ ID NOS: 33

<210> SEQ ID NO 1
<211> LENGTH: 949
<212> TYPE: DNA
<213> ORGANISM: Listeria monocytogenes

<400> SEQUENCE: 1

```
ataggagacg atttaaatgg ttgcgtatgg tgagttaatt cgcgaagtac ggctttcaaa      60
aggactaacg caaaaagaag tttatacagg agtaatttca aaatcatatg caataggttt     120
tgaaaaagga aaacatgata ttacattagt actatttgaa gaaattttag aacgggtcat     180
gttaagttca gatgaatttt tctttatgaa taggggctat tctttagcgg aggaagataa     240
tttttggtac aaatttgcaa atgcagctaa tcaaaaaagt ttggcagaat tacaagaatt     300
ataccaagaa gtattgcagc aaaatggcga tagagcgaat ctaaggaaag caattgtcca     360
ctcgagaatt gaattaatg aacaatttct tttgaataat cgatttgacg ttagtatcgt     420
ttctgaggaa gataaagcag ttatccaaac gtatttgtgg aaagttcaat catggacact     480
agaagaaatt cggatttcg ctaattcagt ggactatttt gaagaagatg tacaaattta     540
tttttttcaa ttggtcttga agtcactcga aaaatataag cattacgatc gtggtaaaaa     600
agtattttcc acgctactca ccaacataat agaagaacta atcacccgtg atcaattaga     660
atatgccgcg caattattag aaatactgca cgaactttct tctacgcatg actgtgcttt     720
ttaccggatt atgcataatt actatcaagg cttaatatgg atgaaaaatg acgaggtcga     780
acaaggctta aaagagtcta aagtgcaat ccgaattta gatgcacttg attacaaatc     840
cctcgcgcta ctttataata cattacttca acagttttta gaaaaagaga atatacaaat     900
agtttaaagt aaatcagata cctttttataa ggtatctgtt tttttggtc                949
```

<210> SEQ ID NO 2
<211> LENGTH: 1470
<212> TYPE: DNA
<213> ORGANISM: Listeria monocytogenes

<400> SEQUENCE: 2

```
tggagataaa aaaggatgct tactaaaata gctacttatg gttgttgtgc aacaagggat      60
ttgttcaata aagcatttgt tagtgattgg aaaaatcatt ttcaattagt gtcatatcaa     120
cagcattgca gtattgtttc actaatgtca aagccaattg atatcgaact aggagaagaa     180
ctgctgggag agttaagtaa ctttgaaaaa agtgtattta aacaagacgt attaaaatct     240
tttttagaaa ctttaaaaac aactcaacca gaatatttag tgttagattt tcatgtggat     300
acattcaatg gttttattga actcactgat gggggattta tcactaatcg aatcgtccgc     360
tataagaaat tggatatttt taataaaatg gaagcaagga aagttttttc gccgttagaa     420
```

| | | | | |
|---|---|---|---|---|
| aatacgactg | agtttagaaa | acgttggata | cagagtttta | accgttttat gcaatttatg | 480 |
| aaagaaaatt | gccctaatac | ccaaattatc | attaataggt | tagaggttgc acgaatgtat | 540 |
| tattctttag | ataaccaaat | ggaaagcatg | atagaacga | gaaaaacaaa agatcaccat | 600 |
| actgctgaga | cattagctaa | aattgatgag | tgcatagatt | actttgagcg ttatgctatg | 660 |
| aataattttg | atttacagtc | attggacttt | aattccgaag | atactttgg tgcagaaaat | 720 |
| aatccatggg | gaacctgtta | tatgcattac | aatccctatt | attataaaaa aagtttaaa | 780 |
| gatttatgga | atatagttga | aaatcatttt | catgcaccaa | caaaattagc tagttttgca | 840 |
| cctggaggcc | ttgcgaaaca | aattccatta | ggtgtgacca | aattatctga tatggatgaa | 900 |
| gtaggagtat | attatttaac | aaatgctact | tacttacaaa | tggaggatcg accgacaaca | 960 |
| gataatgcag | gttatttttt | cattgtttat | ccgcgaaatg | ggaaaaatgg gtatatgcaa | 1020 |
| gagctgagaa | atcaacagc | agctttttcc | attcaaattt | ttgtccgaat tactgatgga | 1080 |
| aaagagagtt | ctaaatggaa | catggtaaat | agtggctttc | gaacacttac aatacctgat | 1140 |
| gtgacttcta | tttctgaaat | tacagaggct | ggagaatatt | atattactgc agaacaggtt | 1200 |
| aagaaacttc | aggatcatcc | tacaaagaaa | aatggttggt | ttctaaccgt ttctaagaaa | 1260 |
| aatcatgata | gcctaaaaca | attgttaaca | aaaaatactc | aaaatgacaa tgcctttgaa | 1320 |
| gaatatgttc | gacttgtaaa | cgtggaaaaa | agaacaaact | taaaatggcg taaatatcat | 1380 |
| tttgatgaag | caaacttttc | gattatagtt | gctatacgta | actttaaaaa caaagtggta | 1440 |
| cgaagattaa | aattaacaaa | agcataaaca | | | 1470 |

<210> SEQ ID NO 3
<211> LENGTH: 730
<212> TYPE: DNA
<213> ORGANISM: Listeria monocytogenes

<400> SEQUENCE: 3

| | | | | |
|---|---|---|---|---|
| aggagagatt | tttatattaa | atcaaaaata | tcaattacta | cttcataatg aatatgacac | 60 |
| aaaaagtggt | gatttagtca | aaaagaaat | agttgcaact | aaaaaaacta aaaatctctt | 120 |
| ggaagatcta | acttcgcatt | tgttatgtgt | tacaaatcaa | atagagtatg gaaaatttat | 180 |
| cacttggtat | gaaatggaaa | ttaaaaaagt | tctacaagtt | catcccaatc agcactttat | 240 |
| tattaaaatt | tcctttcaac | aattatattt | tcgggaaaca | atgctgttgc ttgagaattt | 300 |
| acagaaagat | agccggcgac | taacgattga | gctagtgga | gatagtcaga ttagccctta | 360 |
| ttcaaaggaa | catttttccg | cagaggacag | tgatgctttt | ttgaaaggga agttaaaaat | 420 |
| gttgaaaaag | tggcattatt | ttatttcaaa | gcatattgaa | agtggtgcca tcgaacaaac | 480 |
| actgattttt | acgccctata | ttgatgaatt | gaaatatagt | ttaacgcaaa agtcgaagct | 540 |
| cttacacaat | attactgaat | taaagttttt | tctatcattt | tggaaaaatt gggctgagct | 600 |
| tcgatttgtt | gattttttag | ttttagtaga | tgaaaaaaac | gaatttgtat cgcatgtgct | 660 |
| tttaccagat | gaattaaatg | tacgttgcaa | aatgtatgag | actttggag gaatggtcag | 720 |
| tgagtaaaaa | | | | | 730 |

<210> SEQ ID NO 4
<211> LENGTH: 810
<212> TYPE: DNA
<213> ORGANISM: Listeria monocytogenes

<400> SEQUENCE: 4

```
aaaaactgtt ctaaaaagga gggggaacga tgaaaacgaa gatgccggaa atgctttctt      60
tcatttcaga agaagctgtt agtagaaaaa tgacaagtga ggaaattgct gctcactttg     120
gttatgataa acatcacttt agtcgaaaat ttaaagaaat taatggattc agtgtggttg     180
aatttctttc tagtttaaaa gtggaaaagg cgattattga acttgatgaa gaagtacgca     240
tactcgactt acaagaacat tcaggttttg aaagtagtgg tagtttcaca aatacgttta     300
aaaaatatac aggtagttct cctagaaaat acaaaaccga aatgaatgat atttttatg      360 atatgaaacg ttttgaaaat gataataagg ataagtcaat agcgcatttt caagaaaata     420
atgattcttt ttgcaatgta actattgatg tacctgatga atttgagaag ggtatcatat     480
ttattggact tttccgtact cttataccga atcatatgcc tatatcggga ttagctacta     540
aaaatttaat aggaaatcaa ttgaaaaata ttccaagcgg agactattat ttattagctt     600
gtgcgataag ccagtctaat aacattctat cttattttaa cttaagtaat agtttgagag     660
ggaaagaaga tgaaaagcta tcttttccta aatgttctgg caatcattac gcgattaagc     720
tgagaaaacc aataccagaa gatccaccaa tattagctaa tgtgggaaaa attttaatct     780
cctgtttgaa gaacacaatc tagaacaatt                                      810

<210> SEQ ID NO 5
<211> LENGTH: 960
<212> TYPE: DNA
<213> ORGANISM: Listeria monocytogenes

<400> SEQUENCE: 5
aaacaaattc attaatcatt ttaagcacct ccatatcatt agtttaacaa agcatttacg      60
tttttcattg tatatttgcg acattttgca gaaaaatttg cttcatttct tctggggtat     120
gattactata tcgtttaaat tgtttaatta agtgagcctg gtccgtaaac ccatgaagat     180
aagcaagttc agcgcccggc acacttggat tctcatataa tgcctgtaat acttttttgga   240 aacgaataag ttttgctgtc tgtttaggtg caagtcccat gtgttttttga aacagccgtt   300 ctaactgccg aacagataca gctcctaaca caaattgatt gggttttttgt agtaacttat  360 caatactgtt taaaaaatca ggatggactt gcttgccaag catcattaat tttcgcagta     420
aaaattcttc taataaagct attctttcac tgttcgtcgt catttcagca aacctctctt     480
gaaaaaacga aacaaatcca gcaaacatct cttccggctc ttttacccga ttcatgctac     540
cagtcaagtc ctgttcgaca aataaaaata acgaccacgc ataaaatcgc acggcaaaaa     600
gctcggtatt actttcatcg tcagactcaa acgatgcatc actaacgcca acaaatatag     660
catccgtcac tagccctgtt ttactatcaa ttgtaaaaat aatatccgca cataaatcag     720
gaaccactaa attatttccc gggaaattct tatcatctgc ctcccaaaaa cagcgaatat     780
agcctgtaag agctgcactc ggtagatatt ctttatagcc agcacgcttt ggtgtagcta     840
caatgggata aaacgtttct agcttagcca taaagagacc cccttttcct catagtacca     900 caaaatttc tctttaatca tgcttctttc ttttatttat gggtattaag taaataaggg      960

<210> SEQ ID NO 6
<211> LENGTH: 390
<212> TYPE: DNA
<213> ORGANISM: Listeria monocytogenes

<400> SEQUENCE: 6
ggagtacacc cgatagcaag gaggaactag atgtatatta aagattttgc cactaaaacg      60
gggctttcga ttgatacgct tcgatattat gaggaagaaa aattattaat acctgctaga    120
```

```
aatgaaaaaa attatcgtgt ttatacggaa gaagattact gctgggtaca gcttttactt      180
aaaatgaagc aaacagagat gacaataaca acattaaaa attttgctac attacaaaag      240
caaggagata aaacactccc aaatcggata caaattttag ataatcatat ggaaaacttg      300
tatgaacaac agaaagattt agcagaaacg atttcttttg tggctaaaaa agtggatggg      360
tatcgagaga agttataaaa acaacaggaa                                       390

<210> SEQ ID NO 7
<211> LENGTH: 4470
<212> TYPE: DNA
<213> ORGANISM: Listeria monocytogenes

<400> SEQUENCE: 7
aagtcttgaa aagaaatttt agtatagtta ttatcagtgt attgttactt ggttatttag       60
cgccttttga tactttgtta gtaggtgcag atgaaacaac ggtttctgaa gatacagcag      120
ttaaaacggc agaagcagat agtgctactg aaggcataga aagcgaaaca ggttcagatg      180
atgaaacggc agaagagcca aagaagcaa aagaggcaga agcaagcaaa gaaacgacag       240 aaaagagga aaaagcgaaa acggaagaac cggcttctaa tattaaaacg gagattaata      300
cagataaaag ccagctgaaa caaactagct aaaagcagc ggtgccagca ggaagtacat       360
ataattcttt gtttccagac gacaatcttg ctaaaaaatt agctgtgatt atcacaggaa      420
atgcggctgc aacaggtaat gaatcagtgg atagtgcagc tcttttagca ataagccaac      480
ttgatttgag tggggaaacg ggcaatgacc caacggatat ttccaatatt gaaggattac      540
aatatttaga gaatttaaca agcctgaatt taagtgagaa taatatatcc gacttggctc      600
cacttaaaga tttggtaaac ctggtttcac ttaaccttc ttccaatcga acattagtaa       660
atctttcagg ggtggaggat ttagttaatt tgcaagaact taatgtctct gcaaataagg      720
cgttagaaga tatttcacaa gttgcatcgt tgccagtgtt aaaagaaatt agcgcgcaag      780
gctgtaatat taaaaccttg gaattaaaga atccggctgg tgctgttttg ccagaactag      840
aaacatttta tttgcaagaa aatgatttaa ccaacttaac ttcattagcg aaacttccaa      900
aattaaaaaa tctctatatt aaagggaatg cttcttttaaa aagtttagag acattgaacg      960
gggcgacgaa gctccaattg attgatgcga gtaactgtac cgatttagaa acgcttggag     1020
atattagcgg gctttcggaa ctcgaaatga ttcaattaag tggttgtagt aaactgaaag     1080
aaatcacaag cttgaagaac ttgcctaatc tggtgaatat tacggcggat agctgtgcaa     1140
ttgaagattt aggaacactg aataatttac caaaattaca gacattagtt ctttcagaca     1200
atgaaaattt aaccaatatt actgcaatta ccgatttacc acaattaaaa acattaactt     1260
tggatggctg tggaattaca tctattggaa cgcttgataa ccttcctaaa ttagaaaaat     1320
tagatcttaa ggaaaatcaa ataactagta taagtgaaat aaccgactta ccgcgattaa     1380
gctatttaga tgtaagtgta aataatctta caaccatagg ggacttgaaa aaattacctc     1440
tattagaatg gctgaatgtt agttcgaata gattatcaga tgtgagtaca ctaacaaatt     1500
tcccgagttt aaattatatt aatatatcaa ataatgtcat tagaacagtc ggtaaaatga     1560
ctgaattacc ttcgcttaag gaattttacg ctcaaaataa cagtatatca gatatttcga     1620
tgattcacga tatgccgaat ttaagaaaag tggatgcgag taacaaccta attacaaata     1680
taggtacctt tgataattta ccaaaattgc aaagtctaga tgtgcattca aatagaatta     1740
caagtacatc agttatacat gatttaccaa gcttggagac gtttaatgcg caaactaatt     1800
```

```
tgattaccaa tattggtacg atggataatt taccagattt aacctacgta aacttatctt    1860
tcaacagaat accgtcgctt gctccaattg gtgacctacc caatttagaa acattaatag    1920
tatcagataa taattcttat ttaagaagcc taggaacgat ggacggtgtt cctaaactga    1980
gaattttaga tttacaaaac aattacctta attacactgg aacagaagga aacctaagtt    2040
cattaagtga tttaacaaat ctaacggaat taaatttgcg aaataatgtt tatattgatg    2100
atataagtgg actttccacg ctatcaagac tgatctactt gaatttagat tccaataaaa    2160
ttgaagatat ttctgcattg tctaatttaa cgaatcttca agagttaaca cttgaaaaca    2220
acaagattga aaacatttca gcacttagtg atttggaaaa tttaaacaag ctagttgtat    2280
caaaaaataa aattattgat attagtcctg tcgctaatat ggttaatcga ggggcaattg    2340
taactgcgag taatcaaaca tatacattgc caactgtatt atcatatcaa agctcgttta    2400
ccatagataa tccggttatt tggtatgacg gcacactact agcgccatca tccataggaa    2460
actctggtaa ttacaaggac gggaaaataa cttggactaa tatgaccgct acgtctagtt    2520
ccactttatt taactttaat aggttaaaag acggtttaac cttctcagga acagtcaccc    2580
aaccttataa atctgcagcc aaagtaactg cagatgcaga gcaaacttat acaattggtg    2640
atactatttc agaggagcag ttttttaaaag atgttaatgc aaaatcatca gacggggcac    2700
ctgttacaag tgattttgct acagtggtgg atttaaacac ttttggcgaa tatgaagtta    2760
ctttaacttc cgaaaaagat ggaatccaag gggatagttg caagtaatt gtcaaagttc    2820
ttcacggagc gcctgtcatt tcggcagacc aaacaattag ttatgataaa catgcaacta    2880
ttacagagaa acaattttta gaagatattc atgccagcac agacttggat acagctatta    2940
caaccaattt tagtacagca gttaacttga ataaaggcgg agattataca gttgcactaa    3000
actctgaaaa tgaggacggc gtgaaagctg aaacggttta tgtcactgtt actgtaaata    3060
aagacccagc gccgattata agtgctaaga cagaaatcac gtatgataaa ttctcgaaaa    3120
aaaccgaagc ggcgttctta gatgatatag acgcagatac aaatgatggc tctatagtaa    3180
cttctaattt tgctacagca gttaatttag ataaagctgg tgattatact gttcactga    3240
attctattaa tagtgatggt gtagcgggca cgccaacagc gattattgtg catgtggaga    3300
aagagaaaat agcaacaatt agcacaaata cggcacaaca atatgaaaaa tatgcgaaga    3360
ttaatgaaac gcaatttcta aaagatgttc atgctagtat taacgcgagc ccaacaaccg    3420
cagtttggga aagtgatttt gaaacagtag ttaaactaga cgtcccagga acgtacacag    3480
taacgattac tgctacaaat gaagatggcg gagtatcggc acctaaagaa gtttctgtca    3540
tagtaaggaa aattccagca ccagagatca ctgcagataa ggaaataact tatccgaaat    3600
ttgatgaagt aagtgaagca gaatttttaa atgatattca tgcaactatt agtgacaaaa    3660
atgtagcgat tacaagtaac ttcagcacag atgtgaattt aaataaagct ggcgattaca    3720
cagtaacatt aaatgctacg aatgaagacg gcgtaaaggc tacaccggtt gaagtaattg    3780
tacatgttca acaaggagaa cgccctgtta taacagccga tgcaactatt tcctatgaca    3840
agttcgctaa cataacggaa gcgaagttct tagaagatat tcatgcaaca agtagtgatg    3900
gtcaaagctc tactgtaatc acctctaatt tccagaccgc gacaaacttc aaaacagcca    3960
tgagctacac agttacgctt aatgctgtaa atgaagacgg cattagcgca gaaccagtag    4020
cagtgaccgt tacaataaat aaagaaccag ccgcggcgtt aaaagctgat gcagaagtaa    4080
gctatgcgaa aaatgaagct gtaaccgaat ccgatttctt caaagatgtt catttagaag    4140
gaacggaagc gccaagtaca gccaaagcaa caagtaattt tgattccgta gtagatagaa    4200
```

```
gtaaaacagg agattatact gttacgataa atgctacaaa cgaagatggg gctgtttcta    4260
caccaattga agtaattgtt catattgaag cagaaagtgc accagtaatt acagcgaatg    4320
cagaagtaaa atataacaaa catgaacaaa cagacgaaag aagatttta tatgatagtg     4380 aagcaaaaat cgatgaagct aatgtggaaa ttaaaaccga ttttgcagaa aaagtagata    4440
ttaataaagt tggaacttat actgtcacac                                     4470
```

<210> SEQ ID NO 8
<211> LENGTH: 1190
<212> TYPE: DNA
<213> ORGANISM: Listeria monocytogenes

<400> SEQUENCE: 8

```
gaaaggactg aatacattga gaaaagtttt aatgttttta agcacagctt tattattagc     60
cattctgtca ctaagcttta ctggtttaga tctgaaggca aaagctgctt ctgatttata    120
tccactacct gctccaatta ttgatgtttt cccagatgat ggattagcca agatatggc     180 taaaaactta aacaaagact ctgtgaatga tgttattgac caagatgact ggatgcatt    240 aactggtttg ggatttgaaa caagtacgat tacgaatgat tccatgcaat tactagaacg    300
tgccatgttt aacaatgtca cagatgtaag tattatggaa tttggggcta aactaacgga    360
gttccctgat attacaacca tcccacattt aaaaacgtta ttttttgctg atccacctgg    420
aagattaact agaaacttgt ccctttccaaa ctaccaaaat tatcctgaaa tggataccat    480
tacaatgagc ggaataatt taatcggttc tatccctgat ttcactggaa tgcctgcttt    540
aaaacagctg tatatgtctg aaatgttaat tacaagcgat gaacttccta atttaataa    600 tattccttta cttattacgt tggatctaag ttctaaccaa ttgacaacta ttcctgattt    660
tcaaaatata ccaaatctca catttttaga tttaaatgca aatttattaa ccaatacacc    720
tgattttcaa aatttaccta aattaactga tttaaattta agcataaca atttaactgg    780 tacgatggtt aactacacca acttacctag tttagaatcc ttaaacttag attacaattt    840
tttaactgaa ctaccgtcta atgtattaga taccatctat gttcaaagtc aaaacggaga    900
gcttcctgat caaactatta atcagggcga tacctgtact attgatttac ctatttattt    960
ccaaatggaa gaaactaata tgttagtcag cccagaagtt acgggagaat atatcggat    1020 tagtgtaatc cagcttccga cgacggttaa tgaggaaggc aacaccataa cagtggatac    1080
atccgctcta agtcctggtg agtataaatt agatgtctcg tataatcaca attatgctac    1140
tggaggcgta tgctcttatg attggaatgt aactattaat taatttctac              1190
```

<210> SEQ ID NO 9
<211> LENGTH: 2640
<212> TYPE: DNA
<213> ORGANISM: Listeria monocytogenes

<400> SEQUENCE: 9

```
taaaacggcg tataataaat gattatagag aacgaataag gagtgcgcca aattgaaaac     60
tactaaaata gtaattgcct cattagttag tttaaccatg gtttcaaacc cgctttaac     120 attcgcagca acgaatgatg ttattgataa tacgacagaa atcactactg ataaagaaac    180
aagctcaact caaccaacta taaaaaacac actcaaagcc ggtcaaacac aaagttttaa    240
cgactggttt cctgatgaca atttttgcttc agaggtagca gcagcatttg aaatgcaagc    300
aactgacact atcagcgaag aacaactagc tactctaaca agtctagatt gccataattc    360
```

```
atccataacc gatatgactg gtattgaaaa attaactggt ttaacaaaat taatttgcac      420
aagtaacaac attaccaccc ttgatcttag ccaaaacact aatttaactt atctggcatg      480
tgattcaaat aaacttacaa accttgacgt aaccccgctt acaaaattaa cctacttaaa      540
ttgcgacacg aacaaactca caagttaga tgtaagtcaa aatccactgt taacttattt      600
aaactgcgcg cgcaacacct taaccgaaat agatgtcagc cacaatacac aattaaccga      660
gctagactgc catttaaata aaaaaatcac caaattagat gtgacaccac aaactcaatt      720
aacaacctta gactgtagct ttaataaaat aactgaatta gatgtaagtc aaaataaact      780
actgaaccgt ctaaactgcg acactaataa tataactaaa ctggacctca accaaaatat      840
tcagctaact ttcctagatt gctccagtaa caaattaacc gaaatagatg taaccccgct      900
tacacagtta acatattttg attgtagcgt aaatccttta actgaattag atgtatctac      960
gctttcaaaa ttaactacac tacattgtat acaaacagat ttattagaaa tagacctaac     1020
acacaacaca caattaatat attttcaagc tgaaggatgt agaaaaataa aagagcttga     1080
tgtcacgcat aatacacaat tatatttatt agactgccaa gccgctggta taacagaatt     1140
ggatctttca caaaacccta aattagtcta tttgtattta ataatactg aactaacgga     1200 attagacgtt tcccataaca caaagctgaa aagtttgtct tgcgtaaatg cgcacatcca     1260
agacttctct tctgtaggta aaattcctgc ccttaacaat aatttgagg ctgaagggca     1320 aacaatcacg atgcctaaag aaactttaac aaacaacagc ttgaccattg cagttagccc     1380
tgatttatta gatcagtttg gaaatccgat gaatattgaa ccgggagacg gcggtgtgta     1440
cgaccaagca acaaatacaa taacttggga aaatctcagc acagacaatc cagccgtaac     1500 ctatacttc acttccgaaa acggagctat agtaggaacc gtaacaactc catttgaagc      1560
acctcaaccc atcaaaggag aagacgtcac agtacattac cttgatgaca aaggagaaaa     1620
attggcggat gatgaagttc taagcggtaa tttggacgat cccttatactt ctagcgcaaa     1680 agacatccca gattatacat taacgactac tccagataac gcaaccggaa cattcaccac     1740
tactagccag tccgtaacgt acgtttacac taaaaacatc gtagccgcag agcctgtaac     1800
cgttaattac gtggacgata ctggaaaaac gctctctcca tccgaaatat taaacggaaa     1860
tgttggcgac acttataacg ccactgccaa acaaatcgac ggctacacat tatccgccga     1920
accaaccaat gcaactggac aattcacaag cagcgcgcaa accgtcaact atatttacac     1980
aaaaaatcca gccctgaaa aaggagttgt agaaattcac tatgttgacg aagataataa      2040
acaacttaac tccaccacag aaatttctgg aacaatagga gataactaca cgactgagcc     2100
aaaaactatc gaaggctata cgttaacaac tacaccgggt aatgcaaccg gcactttcac     2160
cacaggcagc caaaccgtga catatgtgta tactaaaaac atcgaagcag cagagccgat     2220
aacagtgaat tacgtggatg ctaatggcaa aacactcgct ccatccgaaa cattaaacgg     2280
aaacgttggc gacacatata agcaactgc caaacaaatc gacggctaca cattatccgc      2340
cgaaccaacc aatgcgactg gacaattcac aagtagcgca caaactgtca actacattta     2400
tacgaaaaac acaaacacag atcaacctt accaactaaa aaacctacga acaccacacc      2460
aaccaagcca tctaatttaa agacaaccga agtgaaaaaa gcttcagata ccctaccaaa     2520
aacaggcgat tccgcaccat ggaaatcagc tctacttggg gtattcctat catccacagc     2580
tctagttatc tggaaaaaga aaaaatagta aaaaagccgg acaggattaa tttcccgacc     2640
```

<210> SEQ ID NO 10
<211> LENGTH: 20

<212> TYPE: DNA
<213> ORGANISM: Artificial Sequence
<220> FEATURE:
<223> OTHER INFORMATION: primer

<400> SEQUENCE: 10
ggctattctt tagcggagga                                          20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
agtagcgcga gggatttgta                                          20

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
tttcgccgtt agaaaatacg a                                        21

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
ttcggacaaa aatttgaatg g                                        21

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
aacttcgcat ttgttatgtg ttac                                     24

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tcactgacca ttcctccaaa                                          20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16

-continued gggaacgatg aaaacgaaga                                              20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
tggcttatcg cacaagctaa t                                            21

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
cggcacactt ggattctcat                                              20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
agggctagtg acggatgcta                                              20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
acccgatagc aaggaggaac                                              20

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
aacttctctc gatacccatc ca                                           22

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ccgatttaga aacgcttgga                                              20

<210> SEQ ID NO 23
<211> LENGTH: 20
<212> TYPE: DNA
<213> ORGANISM: Artificial Sequence

```
<220> FEATURE:
<223> OTHER INFORMATION: primer

<400> SEQUENCE: 23
ttcggcatat cgtgaatcat                                                     20

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
tgattccatg caattactag aacg                                                24

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
aggattctaa actaggtaag ttggtg                                              26

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
tgtaaccccg cttacacagt t                                                   21

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ttacggctgg attgtctgtg                                                     20

<210> SEQ ID NO 28
<211> LENGTH: 540
<212> TYPE: DNA
<213> ORGANISM: Listeria monocytogenes

<400> SEQUENCE: 28
aaaggcggtt atctctaatg ttaaacgaaa atattaaagc aatcagaaaa tcaaaggac          60 tttcgcaaga agaaattgcc atcaaactga atgtggtgcg acaaacaatc tctaaatggg        120
agcaaggact gtcagttcct gattccgata tgttaatctc catatcggaa gtgcttgaaa        180
caccagtaag cactttgctt ggagaaactg ttatggtttc aaaggttgat gatgtaaaag        240
caatttccga aaaactggag attataaact tacagtttgc tcaaagaaag accgccagac        300
gaaaaatgct ttattggcta tttgtctcgt tgtgtgccgt tatagcaata atttctgcgg        360
tctttataat actaaatagt ccttacttag gttgggatta tagtgatcct gaaactagcg        420
ttatcggagt agcttttcat acatttgaat ggttgtttgt cagattagca ccgattatcc       480
```

-continued

| ttataggagg agtcgttgga attttctaa cgcggaagaa cgtataaaat cgtactatgt | 540 |

```
<210> SEQ ID NO 29
<211> LENGTH: 1080
<212> TYPE: DNA
<213> ORGANISM: Listeria monocytogenes

<400> SEQUENCE: 29
```

| aaagcattac aagatttct taaataaata aagcaaaaca cggaaatcca ttcttcggat | 60 |
| ttccgtgttt ttagatga aaaaagcat taactttcgt aaattgagac tatatcataa | 120 |
| attctacgct tcatttttc acgaacatgt aatggctcta acattcgca tttatcgcca | 180 |
| aaactcaaga gaatatcata gtgatactcg ttttctataa aggaaaact gacaatgtaa | 240 |
| tgctcctcac catcgggata aaatttca taagagcaat aatcaagcac tctatcgata | 300 |
| atggattgat gaatacgaat ttaatttct atctgcataa ttgctacaat atcttccatt | 360 |
| tctaactgtg gcttttgaaa atctcgcagt gtaaaagtgt cctcaagtat ttgcagacca | 420 |
| gacatacgag ataacctgaa taaacgaaaa tcattcctat tttggcaata cccatacaaa | 480 |
| taccagtggc tgcttttcat tacaagctga tatggttcaa ctattcttac ggtcttattt | 540 |
| ccttggtgag ctatatattc aaaggttagt aacttgtttt cctgcaaagc cactttgata | 600 |
| atttctacat gtggttgtat gttgttattt cccgtccact ggcttaaatc tatataaatt | 660 |
| tggttcgctt ttagctcgat ttcttttgct ctatcagctg ggataaaact ttttatttt | 720 |
| gcaagagcat ttatcagttc atctccgcgt accatgttag aaagacttga aaggcccata | 780 |
| agaatagcgg aaaggtctgc tgttgaaaaa accttgctat ccatcttgta gtcaggcata | 840 |
| atttcaaacc cgccacctac gcccggtgtt gaacgaatag gtacaccagc caagtcaatc | 900 |
| gcgtctatgt cacgataaat tgtacgaagc gaaacttcaa atctatcagc taactcttgt | 960 |
| gcgctaatac gttctttatc aaggagaatt aaaacaatgc tcataagcct atcaactttc | 1020 |
| atataatagc caccttcaa aattactata tattgttgcc ataatggtgt caacaatcgg | 1080 |

```
<210> SEQ ID NO 30
<211> LENGTH: 772
<212> TYPE: DNA
<213> ORGANISM: Listeria monocytogenes

<400> SEQUENCE: 30
```

| gatctgcatt gtaaacgcca tccacattgt tcttcgccat taaatcacg tctgcttcaa | 60 |
| tttctgctgc ccgaagcagc tgcagttgta tctgtcgaga aatatggatt tcccgtacca | 120 |
| ccagcgaaga ttacgacacg tcctttttcc aagtgtctga ttgctttccg gcgaatataa | 180 |
| ggttcagcga tttggcgcat atcgatagaa gtttgtacac gtgttgctac cccaatattt | 240 |
| tccaaggaat cttgaagaga taaggaattc atgaccgttg caagcattcc catataatct | 300 |
| gctgctgcac gatcaaggtc aatcttaccg gtcagttctt aggtcttaaa tatgtgctac | 360 |
| ctatttaac gaaacaagga aatggaagcg ttatcaacac ggcttctgtg gccggacttg | 420 |
| atggcagttc cttttagcg ccatatgtgg cttcaaaaca cggcgtcagt ggtctgacaa | 480 |
| aagtccgcag cactagaagt agcggataaa ggtgttcggg tcaactccgt ccatccatca | 540 |
| ccagtcaata cccggatgat gcgatcgatc gaaaagaatc tcaacccaga cgatgcggaa | 600 |
| aaagcaaaag aagaatttac aaaagatatt ccagtcggaa gatatgcaga agccagcgat | 660 |
| gtcgcgaaac ttgtccttatt cctagcctcg gacgatagca aatttatcac tggtgcgcaa | 720 |
| tacgggtaga tggcggtatg ggggctacac aataaaatta aaaataaga tc | 772 |

<210> SEQ ID NO 31
<211> LENGTH: 1377
<212> TYPE: DNA
<213> ORGANISM: Listeria monocytogenes

<400> SEQUENCE: 31

```
gatcttgtag ccgatataat aatctcgtaa tttgttgttc attaagcata tttatagaac      60
ctcccataat gaatgcgctg gcatacagat tattatagca tggcttcatt tgtttatcac     120
gaattcctta ttcacttgag ctatttattc tagtctttt ttagaacatt tttactttct     180
atagagaaaa ttactacttc aaggcttatt actaagcaat aattaattta ctaaaaatgg     240
ctttatacca atattcacct gttttttccgt tttttaaaaa caacttttcac taaaaacaac     300
ttcacaattt ttacacattt aaccaactaa gtaaaaatcg ctatatatca gtcatttaac     360
caatttttaa tttttcgtta tacaattgta atagattttt tttcttgttt tttgatatta     420
taattacaaa tagataaaaa aggagtgctt agaactgtgg ataaaaagtt tatgaaatca     480
gggattatta tactcattgt ggcatttatt gtagtttcaa tgaatgttgg agcagaaacg     540
ggtgataatc aggtttctca agttgagtta agttcgcagc aacaagcatt tattaatgaa     600
attttacccg ctgctcaaga tggtctacgt gacggaaagc ttttagccag tgtaacactc     660
gctcaagcta tattggaatc taattggggt gaaagtggtt taagcaaaaa ctcgaataat     720
ttatttggta ttaaaggttc gtataatggg aaatcagttt cgatgcgtac gatggaagca     780
actggggcaa caactgcgaa tttccgtgtt tatcctagct ggcaagaatc cattaaagac     840
catactgatt taattacaca caacgcacgc tataaaggcg cagtcggcga aacagattac     900
cgcaaagcta tacaagcaat taagatggt ggttatgcga ctgatcatgg tgcagaaaca     960
gtagaagtta gacgcaaaaa tggtaagaac gaaacggcaa ccattaattt gaaagccttt    1020
catagtggta ataatgttgt tatcgaaatt gtagatgatg gtgctggtat taacaagcga    1080
aaagttttag agaaagcgat tacgaaaaac gtagtaacga gagcagaatc taccaaaatg    1140
acggatagcg aaatttttga tttgctgttt gactcaggat ttagtaccgc tgatctaaag    1200
ctttttcggct ccctaaaaac tatccgtgcg gaaaaagact ataaaaaagg attacaagtg    1260
cttgataaaa acttttacgg caccatttcc gactttgatt tagaatagaa gtggccgatt    1320
atgtcaaagg taagaaaatt ttcactaaat tattaaaaga ttatcaaata acagatc       1377
```

<210> SEQ ID NO 32
<211> LENGTH: 1537
<212> TYPE: DNA
<213> ORGANISM: Listeria monocytogenes

<400> SEQUENCE: 32

```
gatcatttat cgtatcaaca tcccgttaga ttttcatttc cggaaaggat taatgtttcg      60
taatttcggt agatttttcta atgtccccaa atcttctatt atcgcaatta ttgcagtaat     120
attagttaaa ttaggtagat ttttttaaatc tgtaatttct tttaacttac tacaaccact     180
tagttgaatc atttcaaggg tatgtaatcc cactaatgtc tccaactgtc tccatatccg     240
tacagttact cgcatcaatt aattggattg aggtagaacc atttaatgtt tctaaacttt     300
ccaaagaaga atttcctttg atataaagat ttttcaattt tggtaatgtt gctaatgcag     360
ttaaatcttg caagtcattc tcttgtaaat aaaatgtctc tagttcaggc aaagcatcct     420
cccgcaggat ttttcaagtt ctaatgtttg aatgtttaca acccttgcgc actgatttct     480
```

-continued

```
ttcaaggctg gtaacggctg ctactggtga aatatcagct aaagattcta ccaagttgat      540
acatttaaaa tcctgtaaac tggggtaaac cttcccacac ccgtttaaag tcttctaaaa      600
ttttggtctg gaagaagaga tttattagcc accttatttt ccgttaaacc agtcaagtcg      660
gtgagacatc agttagggtg aatttctcac taaaatttaa cctccgttta ccgtattcta      720
aaatactaga aaccccctta attactcccc aaactcaaat gtctttgcac caagcccgtt      780
tcccgctaaa ttagtgggga ggaaaaagtc ccgcgatttt ggtaatttat cacaatggga      840
gggcttccca ggaggaaaaa gcaattttt gccaagattt tcatctgtaa caaagaatta       900
tatgtactcc cagcaagaac atctgttttt aatttagatt gctttgaagt tggttttctg      960
tttttggttc taatttagga gtgacggctt acttctttcg gatctgtagg ttttccgcc     1020 tcttgttcta atggttcttc tttaacttct gtaatctgaa ttagtttcaa taaccggtgt     1080
tttttcttca gttatttctg attttgtcgt taaatcttca ggaacagttg tttcttccgc     1140
gacggctaaa gtactaaatg gagccaaata ccccaacaaa agagcactaa caattaccat     1200
actaagtttt ttcttcaaga cttttccctca tttcgttcaa attaatttaa cattttttgg    1260
tgctccattt attatacatg gcttgaatac gccatttgtc ttttttaaaat acttatcaaa    1320 acagaaatat gtagatttta tgtcgccaga aaaactagtt tttttaaaac gagctagaat     1380
gttgctctaa tgctattttc actcaaaaaa aacaagccag ataatttcgg cttgtttcga    1440
tgtttatatt attcattttt attttcgat aactactgga ttttgtacat gtacgacttc      1500
aaagcgagca atttcattgc cgacaattcc tttacga                              1537
```

```
<210> SEQ ID NO 33
<211> LENGTH: 825
<212> TYPE: DNA
<213> ORGANISM: Listeria monocytogenes
<220> FEATURE:
<221> NAME/KEY: misc_feature
<222> LOCATION: 610
<223> OTHER INFORMATION: n = A,T,C or G

<400> SEQUENCE: 33
```

```
cattggtgtc cttttagctg tgtggttaat gtgtgtgctc gagaaaaact tgcgtaaaat       60
aattccgaat gcgatagata tcattttcac tcccacattg gtgctactca ttattggtgt      120
agtaactatt ttcttaatca tgccattcgc cggacttgtt tctgatggat tagtgaacgg      180
aatcaactgg gttatcgaag ttggcggtgt ttttgccgga tttgttcttg gtacattatt      240
cttaccaatg gtcatgtttg gtttacatca agttttaaca ccaattcatg tagaaatgat      300
tgcccaaagt ggttatacaa tattattacc gattttagca atggcaggtg gtggacaagt      360
cggtgcatcc atcgctcttt ggattcgttg tcgtaaaaat aaaccacttg ttaacatgat      420
taaaggtggc cttccagtag gtattttagg aattggcgag ccattaattt atggagttac      480
cattccactt ggtagaccct ttctaactgc ttgtcttggt ggtggtattg ggggcgcagt      540
gattggattc ttcggaaaca ttggttcgat tgccattgga ccttctgggg tagcgcttat      600
tccattaatn cgctaacaat gaatggttgg gatatatcat tggtctagta gctgcatatc      660
taggcggatt tatcttaacg tattcttgt acgccaaaag atgcgatgca aatgtggaat       720
ataaactaag ttgactaatc aaagccatta aatgatttat tatttaatgc cctttactat      780
ttacaataag caatttaaat gtaaaatcaa agaaagagtt ttgac                      825
```

USE OF NOVEL VIRULENCE-SPECIFIC GENES AS TARGETS FOR DIAGNOSIS AND POTENTIAL CONTROL OF VIRULENT STRAINS OF *LISTERIA MONOCYTOGENES*

This application claims priority from U.S. Provisional Application Ser. No. 60/444,201, filed Feb. 3, 2003; U.S. Provisional Application Ser. No. 60/447,297, filed Feb. 14, 2003; and U.S. Provisional Application Ser. No. 60/458,414, filed Mar. 31, 2003. The entirety of each of these provisional applications is incorporated herein by reference.

This invention was made with Government support under 58-0790-0-120 awarded by the U.S. Department of Agriculture-Agricultural Research Service. The Government may have certain rights in the invention.

BACKGROUND OF THE INVENTION

1. Field of the Invention

This invention involves the use of novel virulence-specific genes of *Listeria monocytogenes* as targets for specific diagnosis and potential control of virulent strains of *L. monocytogenes*. More particularly, this invention provides a PCR or hybridization method, which uses specific primers or probes corresponding to virulence-specific genes for the identification and control of virulent strains of *Listeria monocytogenes*.

2. Background of the Technology

*L. monocytogenes* is an important cause of human food borne diseases world wide. A notable feature of *L. monocytogenes* is that it shows considerable variation in its ability to produce listeriosis. On the one extreme, some *L. monocytogenes* strains are virulent and can result in severe disease and mortality. On the other, some have limited capability to establish in the host and are relatively avirulent and harmless. Because manufactured food products detected with *L. monocytogenes* are recalled or downgraded (i.e., used for pet food), contamination with this species may render significant economic losses. With outbreaks of listeriosis due to contaminated foods on the increase in recent years, *L. monocytogenes* has become a major concern to the food industry and health regulation authority.

Apart from adapting stringent quality control measures during food processing procedures, frequent monitoring with specific laboratory tests for virulent strains of *L. monocytogenes* is vital in reducing unnecessary food product recalls and allaying consumer concerns. The current diagnostic methods are incapable of distinguishing virulent from avirulent strains of *L. monocytogenes*.

The complete genome of *Listeria monocytogenes* EGDe strain was reported recently (Glaser et al., 2001). Although this publication contains a list of all known and putative genes in *L. monocytogenes* EGD strain as well as their nucleotide sequences, it does not provide any information on the actual application of these genes. Therefore, although the DNA sequences of the genes described in this invention have been published and are in public domain through the release of the *L. monocytogenes* EGDe genome sequence, there are no prior publications on the functions of these genes or on their use for research or diagnostic purposes.

Previous research used PCR and DNA sequencing or restriction fragment length polymorphism of the *L. monocytogenes* hlyA, actA, and inlA genes to group *L. monocytogenes* into three genetic lineages, with the various lineages varying in potential for human virulence (Norton et al., 2001; Wiedmann et al., 1997). Ribotyping (sequencing of rRNA genes) was also used in this research. These assays are different from the present assay employed by the inventors in that they require either DNA sequencing or restriction digests following PCR amplification, while the present assay is simply a PCR assay. In addition, the hlyA, actA, and inlA genes are present in all *L. monocytogenes* isolates, while the virulence-specific genes described by the inventors are found only in virulent strains of *L. monocytogenes*.

Another PCR assay, random amplification of polymorphic DNA (RAPD) PCR, has been used to classify *L. monocytogenes* into genetic groups that tend to predict virulence. This technique is based on the use of nonspecific primers that bind to unknown sequences in the *L. monocytogenes* chromosome (Franciosa et al., 2001). The PCR assay employed by the inventors is based on primers that bind to specific virulence associated chromosomal sequences that we have identified.

Other assays have been described for differentiation of virulent and avirulent *L. monocytogenes* isolates. The "gold standard" for virulence testing of *L. monocytogenes* isolates is the mouse virulence test. This test is expensive, labor intensive, requires several weeks to complete, and requires regulatory approval to ensure humane treatment of animals. Assays have been described based on cell culture models; one correlated *L. monocytogenes* virulence with the ability of isolates to form plaques on HT-29 cells (Roche et al., 2001), and another correlated virulence with the ability to cause cytopathogenic effects in Caco-2 cells (Pine et al., 1991). Although the use of cell culture models represents an improvement over mouse virulence testing, it is still time-consuming and labor intensive.

Research has been published on the use of phenotypic detection of virulence factor expression (listeriolysin, phosphatidylinositol phospholipase C, phosphatidylcholine phospholipase C) to separate virulent from avirulent *L. monocytogenes* isolates (Erdenlig et al., 2000). Research has also been published on the use of monoclonal antibodies for detection of virulence factor expression (listeriolysin and phosphatidylcholine phospholipase C) to distinguish virulent and avirulent isolates (Erdenlig et al., 1999). The dot blot hybridization technique described in this invention has also been previously published. For example, this technique was employed to identify virulence and avirulence associated markers of *Dichelobacter nodosus*—the ovine footrot pathogen (Liu & Yong, 1993). Several PCR assays have been described for species specific detection of *L. monocytogenes* (examples include Aznar & Alarcon, 2002; Bassler et al., 1995; Blais et al., 1997; Klein & Juneja, 1997; Norton & Batt, 1999; Winters et al., 1999). PCR assays for distinguishing all six *Listeria* species can be based on the 16S and 23S rRNA genes (Sallen et al., 1996) or the intergenic spacer region of 16S and 23S rRNA genes (Graham et al., 1997), or the iap gene (Bubert, et al., 1999). However, none of these PCR assays distinguish virulent *L. monocytogenes* isolates from avirulent isolates.

SUMMARY OF THE INVENTION

This invention involves the use of virulence-specific genes of *Listeria monocytogenes* as targets for specific diagnosis and potential control of virulent strains of *L. monocytogenes* and overcomes the above identified shortcomings of conventional detection methods.

Using a comparative screening strategy, the inventors isolated two potential virulence-specific clones from a recombinant DNA library from *L. monocytogenes* strain EGD. Specifically, a hybridization technique was used to compare genomic DNA from virulent and avirulent *L.* monocytogenes isolates to identify clones containing genetic markers that are uniquely present in either virulent and/or avirulent strains. DNA sequence analysis of the two virulence specific clones revealed that they contain gene markers that are distinct from the previously reported virulence gene cluster encompassing prfA, plcA, hlyA, mpl, actA, and plcB. By employing primers derived from these as well as other newly identified virulence-specific gene markers, the inventors discovered a method by which virulent strains of *L. monocytogenes* can now be readily distinguished from avirulent strains through the formation of specific PCR products.

The method of the present invention for separation of virulent and avirulent *L. monocytogenes* isolates can be used to provide a scientific basis for the determination of when and if food safety recalls should occur when *L. monocytogenes* is isolated from food products.

In one embodiment of this invention, virulence-specific genes of *Listeria monocytogenes* are used as targets for specific diagnosis and potential control of virulent strains of *L. monocytogenes*.

In another embodiment of this invention, one or more of *L. monocytogenes* virulence-specific genes are used to detect virulent strains of *L. monocytogenes*.

In another embodiment of this invention, one or more of *L. monocytogenes* virulence-specific genes are used to detect virulent strains of *L. monocytogenes* by polymerase chain reaction (PCR) using primers specific for the DNA sequence from the gene(s) or by hybridization using a probe specific for the DNA sequence from the gene(s).

In another embodiment of this invention, the one or more *L. monocytogenes* virulence-specific genes are selected from the group consisting of: lmo0833, lmo2672, lmo1116, and lmo1134 (encoding putative transcriptional regulators); lmo0834 and lmo1188 (encoding proteins with unknown function); and lmo0333, lmo2470, and lmo2821 (encoding proteins similar to internalins).

In another embodiment of this invention, a combination of two or more of *L. monocytogenes* virulence-specific genes are used to detect virulent strains of *L. monocytogenes* by multiplex polymerase chain reaction (PCR) or hybridization using primers or probes specific for the DNA sequences from the gene(s).

In another embodiment of this invention, one or more of *L. monocytogenes* virulence-specific genes are used to detect virulent strains of *L. monocytogenes* by multiplex polymerase chain reaction (PCR) or hybridization using primers or probes specific for the DNA sequence from the gene(s) in combination with *Listeria* genus-specific primers or probes and/or *L. monocytogenes* species-specific primers or probes.

In another embodiment of this invention, the one or more *L. monocytogenes* virulence-specific genes are one or more genes that indicate virulent forms of *L. monocytogenes* or combinations thereof.

In another embodiment of this invention, the *L. monocytogenes* virulence-specific genes or their derivatives are used in the inhibition of growth, reduction of pathogenicity, treatment, or prevention of virulent strains of *Listeria monocytogenes*.

In another embodiment of this invention, virulent strains of *Listeria monocytogenes* are detected by amplification of *L. monocytogenes* virulence-specific genes from mRNA by reverse transcription-PCR (RT-PCR).

In another embodiment of this invention, virulent strains of *Listeria monocytogenes* are detected by one or more methods for detection of protein product(s) from *L. monocytogenes* virulence-specific genes.

In another embodiment of this invention, virulent strains of *Listeria monocytogenes* are detected by one or more methods for detection of protein product(s) from *L. monocytogenes* virulence-specific genes using either polyacrylamide gel electrophoresis, high-performance liquid chromatography (HPLC), mass spectrometry, or antibody detection methods (examples include immunofluorescent antibodies (IFA), enzyme-linked immunosorbent assay (ELISA), or Western blotting).

In another embodiment of this invention, virulent strains of *Listeria monocytogenes* are detected by one or more methods for detection of protein product(s) from *L. monocytogenes* virulence-specific genes by use of assay(s) specific for the function(s) of the protein product(s).

In another embodiment of this invention, the virulence-specific *L. monocytogenes* genes are used as a treatment strategy such that pharmaceutically active agent(s) would inactivate or alter the function of one or more of the proteins encoded by the virulence-specific *L. monocytogenes* genes, which would either kill the virulent *L. monocytogenes* or render it susceptible to the host immune system.

In another embodiment of this invention, one or more of the *L. monocytogenes* genes or promoter(s) for one or more of the virulence-specific *L. monocytogenes* genes is altered such that expression of the encoded protein(s) would be completely disrupted or altered. The said alteration or disruption of expression would render *L. monocytogenes* avirulent and effective as a live attenuated vaccine.

In another embodiment of this invention, the *L. monocytogenes* virulence-specific genes are selected from the group consisting of: lmo0833, lmo1188, lmo0834, lmo1116, lmo2672, lmo1134, lmo0333, lmo2470, and lmo2821.

In another embodiment of this invention, the one or more *L. monocytogenes* virulence-specific genes are one or more genes that indicate one or more virulent forms of *L. monocytogenes*.

BRIEF DESCRIPTION OF THE DRAWINGS

FIG. 1 shows the DNA sequences of SEQ ID NOS.: 1-9 for each of the virulence-specific genes of *Listeria monocytogenes* according to the present invention.

FIG. 2 shows the DNA sequences of SEQ ID NOS.: 28-33 for each of the *Listeria* species-specific gene sequences according to the present invention.

DETAILED DESCRIPTION OF THE INVENTION

*Listeria monocytogenes* is a small gram-positive coccobacillus that tends to form short chains of three to five bacteria. Infections from this pathogen occur worldwide in various animals and man (Gray and Killinger, 1966) and can be fatal in immunocompromised individuals such the elderly, pregnant women, newborns, diabetics and transplantation patients (Gellin and Broome, 1989). *L. monocytogenes* is of particular concern to the food industry and public health regulatory agencies because it can grow at refrigerator temperatures and because it is ubiquitous in nature (Farber and Speirs, 1987, Lamont et al., 1988). It has been found in a variety of foods such as vegetables (Heisick et al., 1989), milk (Donnelly and Baigent, 1986, Doyle et al., 1987), various cheeses (Rodler and Korbler, 1989), meat products (Farber et al., 1989), poultry (Carpenter and Harrison, 1989), and fish (Lennon et al., 1984; Erdenlig et al., 1999).

Of the 13 known serotypes of *L. monocytogenes,* many of which are found in foods, only three serotypes (1/2a, 1/2b, 4b) are associated with the majority of human illness (Schuchat et al., 1991). However, not all strains of these *L. monocytogenes* serotypes are pathogenic, with some strains having either no or low-level virulence (Hof and Rocourt, 1992). Previous work at the College of Veterinary Medicine at Mississippi State University indicated that *L. monocytogenes* isolates from channel catfish vary in virulence using the mouse model, with some isolates being highly virulent and others being completely avirulent (Erdenlig et al., 2000). There is also molecular evidence for the existence of genetic lineages of *L. monocytogenes* that vary in virulence (Norton et al., 2001; Wiedmann et al., 1997). This data indicates that food safety recalls based solely on detection of *L. monocytogenes* without determination of virulence could lead to unnecessary recalls, which would have devastating consequences on food producers and processors. To prevent economic losses due to food recalls, and to reduce human food safety concerns, it is important to understand what causes certain *L. monocytogenes* to be virulent and to devise ways to accurately ascertain virulence.

*L. monocytogenes* is a facultative intracellular pathogen, and some of its best-known virulence factors contribute to its ability to survive inside professional phagocytic cells. After it is phagocytosed, *L. monocytogenes* lyses the host vacuole and escapes into the cell cytoplasm. This step is mediated by listeriolysin (LLO) and phosphatidylinositol phospholipase C (PI-PLC) (Camilli et al., 1993, Portnoy et al., 1988). The bacteria are then propelled through the host cell cytoplasm by inducing the polymerization of host actin, a process that is mediated by a surface protein designated ActA (Domann et al., 1992). The bacteria then apparently spread from cell to cell by inducing formation of pseudopod-like structures containing bacteria that are internalized by neighboring cells. A second phospholipase, phosphatidylcholine phospholipase C (PC-PLC) is required for this step (Vazquez-Boland et al., 1992). A zinc metalloprotease, Mpl, may be required for activation of PC-PLC (Poyart et al., 1993).

The genes encoding these virulence factors are clustered on the *L. monocytogenes* chromosome between the ldh and prs operons: prfA (PrfA, regulatory gene), plcA (PI-PLC), hlyA (LLO), mpl (Mpl), actA (ActA), and plcB (PC-PLC) (Portnoy et al., 1992). This gene cluster is one of the most well studied regions of the *L. monocytogenes* chromosome; there have been numerous publications on the roles that these genes play in virulence (Bohne et al., 1996, Bubert et al., 1999, Freitag and Jacobs, 1999, Kuhn and Goebel, 1995, Smith et al., 1995).

Previous work at the College of Veterinary Medicine at Mississippi State University has shown that expression of LLO and PC-PLC is valuable in indicating the pathogenicity of *L. monocytogenes* isolates (Erdenlig et al., 1999; Erdenlig et al., 2000). Expression of LLO and PC-PLC in seven *L. monocytogenes* isolates were compared, four of which were virulent in mice and three of which were avirulent in mice. Expression of both LLO and PC-PLC was present in all four virulent strains, and expression of LLO and PC-PLC was absent in two out of three avirulent strains (Table 1). None of the three avirulent strains expressed both LLO and PC-PLC.

TABLE 1

Application of mAbs to detect the presence of virulence factors from *L. monocytogenes* channel catfish isolates and their correlation to pathogenicity

| *L. monocytogenes* catfish isolate | Serovar | LLO | PC-PLC | Pathogenicity[1] |
|---|---|---|---|---|
| ATCC 15313 | 1 | − | + | − |
| ATCC 19115 | 4b | + | + | + |
| EGD | ½a | + | + | + |
| CCF 1[2] | 1 | + | + | + |
| HCC 7[2] | 1 | +[3] | + | + |
| HCC23 | 4 | + | − | − |

[1]Pathogenicity data for CCF 1, CCF 4, HCC 7, and HCC 23 are published in Erdenlig et al. (1999).
[2]CCF = channel catfish fillet; HCC = healthy channel catfish organs.
[3]HCC 7 is weakly positive for LLO.

DNA sequencing of the promoters from the virulence gene clusters of these seven *L. monocytogenes* isolates were completed. The promoters that were sequenced control expression of the hlyA, plcA, prfA, and plcB genes. In addition, the entire prfA gene was sequenced from the seven isolates because PrfA binds to each of these promoters to control transcription. The sequences were obtained by first amplifying the regions of interest by PCR and directly sequencing the PCR products.

The sequencing results provide evidence that there are distinct genetic lineages of *L. monocytogenes* based on the virulence gene promoter sequences. Phylogenetic analysis indicated that in three of the promoters, the seven strains grouped consistently into three genetic lineages. In the fourth promoter controlling hly (LLO) expression, five out of seven isolates were grouped into the same genetic lineages. The different groupings of the other two strains at this promoter possibly reflect differences in expression of LLO.

The sequencing results also revealed potential sequence differences that could explain the differential expression of LLO and PC-PLC between isolates. In one isolate that fails to express PC-PLC, two amino acid substitutions were detected in PrfA. In the hly promoter, there were three nucleotide substitutions in the strain that fails to produce LLO compared to other strains. In one of the plcB promoters, there were four nucleotide substitutions in the promoter region of a non-PC-PLC producing strain compared to other strains.

However, the sequencing results also demonstrated that these genes (prfA, plcA, hlyA, and plcB) are not good candidates for the development of PCR-based tests for distinguishing virulent from avirulent strains. These genes are present in all *L. monocytogenes* isolates (and even some other *Listeria* species), and the sequencing results demonstrated that the sequence variations in these genes between virulent and avirulent isolates are too few to allow development of PCR primers that would reliably distinguish virulent and avirulent isolates.

Therefore, the goal was to identify other gene markers that could be used for distinguishing virulent *L. monocytogenes* isolates from avirulent isolates. Although the genome sequence of virulent *L. monocytogenes* strain EGD recently became available (Glaser et al., 2001), the sequence of avirulent *L. monocytogenes* isolates are not available for comparison to identify these unique genes. Therefore, dot blot hybridization was used to identify *L. monocytogenes* virulence-associated markers, which is a technique that had been previously used to detect chromosomal markers that are unique to both virulent and avirulent isolates of *Dich-*

*elobacter nodosus*, the causative agent of ovine footrot (Liu and Yong, 1993). These markers identified from *D. nodosus* were used as the basis for development of a diagnostic test that can be used to differentiate virulent, intermediate, and avirulent isolates of this species (Liu, 1994).

To prepare for dot blot hybridization, genomic DNA was prepared from the known virulent and avirulent strains of *Listeria monocytogenes* using a standard protocol (Ausubel et al., 1994) and suspended in TE buffer (10 mM Tris, 1 mM EDTA, pH 8.0). The purified DNA from virulent strain EGD and avirulent strain HCC23 was partially digested with restriction endonuclease Sau3A I. Digested DNA was separated by agarose gel electrophoresis, and fragments in the 0.5-3 kilobase range were excised and eluted. The size fractionated DNA was then cloned into BamH I digested plasmid vector (pGEM-3Z; Promega). The resultant recombinant DNA libraries were transformed into *E. coli* XL1-Blue MRF, and clones with insert were identified by blue-white screening. Plasmid DNA was isolated from individual clones in batches of 50 using a rapid alkaline lysis procedure. Inserts were isolated by digestion with Pst I and EcoR I, separated from vector DNA by agarose gel electrophoresis, eluted by the phenol-thaw method, and labeled for hybridization using the ECL protocol for labeling double stranded DNA (Amersham Pharmacia Biotech). If inserts contained Pst I or EcoR I restriction sites, inserts were recovered by digestion with Sma I and Hind III.

The dot blot hybridization was conducted using the procedure described by Liu and Yong (Liu and Yong, 1993). Briefly, DNA from each of the four virulent strains and the three avirulent strains were heated at 100° C. for 3 minutes before being mixed with an equal volume of 1.8 M NaCl, 0.18 M sodium citrate and 4.4 M formaldehyde. Fifty microliters of DNA from each of the seven strains (0.5 g DNA/dot) was spotted onto nylon membranes (Hybond-N, Amersham Pharmacia Biotech) using a dot blot apparatus (Schleicher and Schuell). DNA was spotted in 50 panels, with each panel containing one dot from each of the seven strains, and fixed on membranes using UV light in a Stratalinker 2400 (Stratagene). Dot blot panels were separated from each other and individually hybridized with the labeled inserts.

Inserts were identified from these hybridizations that demonstrate preferential binding to virulent or avirulent strains. Inserts from identified clones were sequenced on both ends using primers from the vector sequence. Clones from the virulent strain EGD were easily identified based on the available genome sequence data, but inserts from the avirulent strain required sequencing the entire insert using a primer walking strategy. Southern hybridizations using labeled probes from the identified clones were conducted using genomic DNA from all seven strains to confirm results from the dot blot hybridizations.

Through this comparative screening procedure, two recombinant clones (Lmo2-28 and Lmo2-432) were identified from the genomic DNA libraries of *L. monocytogenes* strain EGD (NCTC7973). Following nucleotide sequence analysis of these two clones and subsequent BLAST searches at GenBank, clone Lmo2-28 was found to contain parts of lmo0833/lmo0834 of *L. monocytogenes* EGDe, which encode a putative transcriptional regulator and an unknown protein. Clone Lmo2-432 was found to contain part of lmo1188 of *L. monocytogenes* EGDe, which encodes an unknown protein. Because of this interesting finding and the fact that transcriptional regulators are specialized DNA binding proteins that play essential roles in the regulation of RNA synthesis and gene expression within bacteria, attention was focused on genes encoding transcriptional regulators in *L. monocytogenes*. As a result, several other genes (lmo2672, lmo1116, and lmo1134) were selected from the list of *L. monocytogenes* EGDe genes (Glaser et al., 2001) for further evaluation (Table 2). Furthermore, because internalins are found exclusively in *Listeria*, additional attention was also directed to *L. monocytogenes* EGDe genes that encode putative internalins. Thus, the inventors selected three genes (lmo0333, lmo2470, and lmo2821) that code for proteins similar to internalins for assessment. The *Listeria monocytogenes* virulence-specific genes used as examples of the present invention are listed in Table 2. Sequence lists for each of these genes are shown in FIG. 1 as: lmo0833 (SEQ ID NO: 1), lmo1188 (SEQ ID NO: 2), lmo0834 (SEQ ID NO: 3), lmo1116 (SEQ ID NO: 4), lmo2672 (SEQ ID NO: 5), lmo1134 (SEQ ID NO: 6), lmo0333 (SEQ ID NO: 7), lmo2470 (SEQ ID NO: 8), and lmo2821 (SEQ ID NO: 9). Primers [forward primers (5'-3') and reverse primer (3'-5')], corresponding to each of the *L. monocytogenes* virulence-specific genes are also shown in Table 2. As indicated in the Table, these primers are sequentially designated as SEQ ID NOS.: 10-27. The oligonucleotide primers, which were designed from each of these genes were assessed in PCR against a collection of 29 *L. monocytogenes* strains (Table 3).

TABLE 2

Identities of novel *L. monocytogenes* virulence specific gene markers

| Gene | Genome location | Putative function | Size (aa) | Forward primer (5'-3') | Reverse primer (5'-3') | Primer positions | PCR product (bp) |
|---|---|---|---|---|---|---|---|
| lmo0833 | 223780-224730 | Transcriptional regulator | 296 | ggctattctttagcggagga SEQ ID NO. 10 | agtagcgcgagggatttgta SEQ ID NO. 11 | 223996-224015; 224633-224613 | 638 |
| lmo1188 | 53621-55085 | Unknown protein | 483 | tttcgccgttagaaaatacga SEQ ID NO. 12 | ttcggacaaaaatttgaatgg SEQ ID NO. 13 | 54027-54047; 54689-54668 | 663 |
| lmo0834 | 224810-225537 | Unknown protein | 237 | aacttcgcatttgttatgtgttac SEQ ID NO. 14 | tcactgaccattcctccaaa SEQ ID NO. 15 | 224940-224963; 225533-225513 | 594 |

TABLE 2-continued

Identities of novel *L. monocytogenes* virulence specific gene markers

| Gene | Genome location | Putative function | Size (aa) | Forward primer (5'-3') | Reverse primer (5'-3') | Primer positions | PCR product (bp) |
|------|-----------------|-------------------|-----------|------------------------|------------------------|------------------|------------------|
| lmo1116 | 262997-263783 | Transcriptional regulator | 257 | gggaacgatgaaaacgaaga SEQ ID NO. 16 | tggcttatcgcacaagctaat SEQ ID NO. 17 | 263006-63025; 263593-263573 | 591 |
| lmo2672 | 25985-26804 | Transcription regulator | 268 | cggcacacttggattctcat SEQ ID NO. 18 | agggctagtgacggatgcta SEQ ID NO. 19 | 26117-26136; 26597-26578 | 481 |
| lmo1134 | 8009-8368 | Transcriptional regulator | 115 | acccgatagcaaggaggaac SEQ ID NO. 20 | aacttctctcgatacccatcca SEQ ID NO. 21 | 7998-8017; 8364-8343 | 367 |
| lmo0333 | 936-6272 | Internalin | 1778 | ccgatttagaaacgcttgga SEQ ID NO. 22 | ttcggcatatcgtgaatcat SEQ ID NO. 23 | 1930-1949; 2569-2550 | 640 |
| lmo2470 | 149254-150433 | Internalin | 388 | tgattccatgcaattactagaacg SEQ ID NO. 24 | aggattctaaactaggtaagttggtg SEQ ID NO. 25 | 149527-149550; 150071-150046 | 545 |
| lmo2821 | 188153-190708 | Internalin | 851 | tgtaaccccgcttacacagtt SEQ ID NO. 26 | ttacggctggattgtctgtg SEQ ID NO. 27 | 188989-189009; 189599-189580 | 611 |

TABLE 3

List of bacterial strains examined by PCR using *L. monocytogenes* virulence specific primers

| Strain | Serovar | lmo0833/ lmo1188 | lmo0834 | lmo1116 | lmo2672/ lmo1134 | lmo0333 | lmo2470 | lmo2821 |
|--------|---------|------------------|---------|---------|------------------|---------|---------|---------|
| *L. monocytogenes* ATCC 19111 | 1 | + | + | + | + | + | + | + |
| *L. monocytogenes* ATCC 19112 | 2 | + | + | + | + | + | + | + |
| *L. monocytogenes* ATCC 19113 | 3 | + | + | + | + | + | + | + |
| *L. monocytogenes* ATCC 19114 | 4a | − | − | − | − | − | − | − |
| *L. monocytogenes* ATCC 19115 | 4b | − | + | − | + | + | + | + |
| *L. monocytogenes* ATCC 19116 | 4c | − | − | + | − | − | − | + |
| *L. monocytogenes* ATCC 19117 | 4d | − | + | + | + | − | + | + |
| *L. monocytogenes* ATCC 19118 | 4e | − | − | + | + | − | + | + |
| *L. monocytogenes* ATCC 15313 | 1 | + | − | + | − | − | + | + |
| *L. monocytogenes* EGD (NCTC 7973) | ½a | + | + | + | + | + | + | + |
| *L. monocytogenes* HCC7 | 1 | + | + | + | + | + | + | + |
| *L. monocytogenes* HCC8 | 1 | + | + | + | + | − | + | + |
| *L. monocytogenes* HCC12 | 4 | − | − | − | − | − | − | − |
| *L. monocytogenes* HCC13 | 4 | − | − | − | − | − | − | − |
| *L. monocytogenes* HCC16 | 4 | − | − | − | − | − | − | − |
| *L. monocytogenes* HCC17 | 4 | − | − | − | − | − | − | − |
| *L. monocytogenes* HCC18 | 4 | − | − | − | − | − | − | − |
| *L. monocytogenes* HCC19 | 4 | − | − | − | − | − | − | − |
| *L. monocytogenes* HCC23 | 4 | − | − | − | − | − | − | − |
| *L. monocytogenes* HCC24 | 4 | − | − | − | − | − | − | − |
| *L. monocytogenes* HCC25 | 4 | − | − | − | − | − | − | − |
| *L. monocytogenes* 168 | | + | + | + | + | + | + | + |
| *L. monocytogenes* 180 | | +/− | + | − | + | + | + | + |
| *L. monocytogenes* 418 | | + | + | + | + | + | + | + |
| *L. monocytogenes* 742 | | + | + | + | + | + | + | + |
| *L. monocytogenes* 874 | | − | − | − | + | + | + | + |
| *L. monocytogenes* 1002 | | + | + | + | + | + | + | + |
| *L. monocytogenes* 1084 | | + | + | + | + | − | + | + |
| *L. monocytogenes* 1400 | | + | + | + | + | + | + | + |

TABLE 3-continued

List of bacterial strains examined by PCR using *L. monocytogenes* virulence specific primers

| Strain | Serovar | lmo0833/ lmo1188 | lmo0834 | lmo1116 | lmo2672/ lmo1134 | lmo0333 | lmo2470 | lmo2821 |
|---|---|---|---|---|---|---|---|---|
| *L. innocua* ATCC 33090 | 6a | − | − | − | − | − | − | − |
| *L. innocua* 415 | | − | − | − | − | − | − | − |
| *L. innocua* 416 | | − | − | − | − | − | − | − |
| *L. innocua* 417 | | − | − | − | − | − | − | − |
| *L. innocua* 662 | | − | − | − | − | − | − | − |
| *L. innocua* 1419 | | − | − | − | − | − | − | − |
| *L. innocua* 1425 | | − | − | − | − | − | − | − |
| *L. innocua* 1720 | | − | − | − | − | − | − | − |
| *L. innocua* 1944 | | − | − | − | − | − | − | − |
| *L. grayi* ATCC 19120 | | − | − | − | − | − | − | − |
| *L. grayi* ATCC 25400 | | − | − | − | − | − | − | − |
| *L. murrayi* ATCC 25401 | | − | − | − | − | − | − | − |
| *L. ivanovii* ATCC 19119 | | − | − | − | − | − | − | − |
| *L. ivanovii* 3325 | | − | − | − | − | − | − | − |
| *L. seeligeri* ATCC 35967 | | − | − | − | − | − | − | − |
| *L. seeligeri* 3008 | | − | − | − | − | − | − | − |
| *L. seeligeri* 3321 | | − | − | − | − | − | − | − |
| *L. welshimeri* ATCC 35897 | | − | − | − | − | − | − | − |
| *L. welshimeri* ATCC 43550 | ½b | − | − | − | − | − | − | − |
| *L. welshimeri* ATCC 43551 | 6a | − | − | − | − | − | − | − |
| *L. welshimeri* CCF4 | | − | − | − | − | − | − | − |
| *L. welshimeri* 1471 | | − | − | − | − | − | − | − |
| *Aeromonas hydrophila* ATCC 35654 | | − | − | − | − | − | − | − |
| *Clostridium perfringens* | | − | − | − | − | − | − | − |
| *Enterococcus faecalis* ATCC 29212 | | − | − | − | − | − | − | − |
| *Escherichia coli* ATCC 25922 | | − | − | − | − | − | − | − |
| *Flavobacterium indolegenes* | | − | − | − | − | − | − | − |
| *Klebsiella pneumoniae* ATCC 13883 | | − | − | − | − | − | − | − |
| *Proteus vulgaris* ATCC 13315 | | − | − | − | − | − | − | − |
| *Pseudomonas aeruginosa* ATCC 27853 | | − | − | − | − | − | − | − |
| *Salmonella typhimurium* ATCC 14028 | | − | − | − | − | − | − | − |
| *Serratia marcescens* ATCC 8100 | | − | − | − | − | − | − | − |
| *Staphylococcus aureus* ATCC 25923 | | − | − | − | − | − | − | − |
| *Streptococcus pneumoniae* | | − | − | − | − | − | − | − |
| *Streptococcus pyogenes* ATCC 19615 | | − | − | − | − | − | − | − |
| *Vibrio cholerae* | | − | − | − | − | − | − | − |
| *Yersinia pseudotuberculosis* | | − | − | − | − | − | − | − |

The results indicated that the PCR primers derived from these genes reacted predominantly with virulent strains of *L. monocytogenes* because the virulence of several of these strains (EGD, 19115, CCF1, HCC7, HCC23 and 15313) was determined previously by mouse virulence assay (Erdenlig et al., 2000). To further verify the virulence of *L. monocytogenes* strains as determined by PCR, a second mouse virulence trial was recently conducted involving 12 *L. monocytogenes* strains (Table 4). The validity of PCR determination of the virulence of *L. monocytogenes* has been again confirmed by the mouse virulence trial. One notable exception is *L. monocytogenes* strain ATCC15313, which is avirulent due to a mutation that causes failure to express listeriolysin, a known virulence factor. The PCR results suggest that the other virulence-specific genes in this strain are intact.

TABLE 4

Summary of *L. monocytogenes* mouse virulence trial

| Strain | Serovar | PCR | Mouse virulence trial | LD50 |
|---|---|---|---|---|
| *L. monocytogenes* ATCC 19112 | 2 | V | V | $1.6 \times 10^9$ |
| *L. monocytogenes* ATCC 19114 | 4a | A | A | $1.9 \times 10^{10}$ |
| *L. monocytogenes* ATCC 9115 | 4b | V | V | $6.0 \times 10^8$ |
| *L. monocytogenes* ATCC 19116 | 4c | V | V | $2.6 \times 10^8$ |
| *L. monocytogenes* ATCC 19117 | 4d | V | V | $8.8 \times 10^8$ |
| *L. monocytogenes* ATCC 19118 | 4e | V | V | $7.8 \times 10^9$ |
| *L. monocytogenes* ATCC 15313 | 1 | V | A | $>1.2 \times 10^{11}$ |
| *L. monocytogenes* EGD | ½a | V | V | $<1.1 \times 10^7$ |
| *L. monocytogenes* HCC8 | 1 | V | V | $<7 \times 10^8$ |
| *L. monocytogenes* HCC25 | 4 | A | A | $3.5 \times 10^{10}$ |
| *L. monocytogenes* 874 | not determined | V | V | $<8.0 \times 10^7$ |
| *L. monocytogenes* 1002 | not determined | V | V | $5.2 \times 10^8$ |

Therefore, the present invention utilizes one or more *L. monocytogenes* virulence-specific genes that allow detection of virulent strains of *L. monocytogenes*. Specifically, these genes include lmo0833, lmo2672, lmo1116, and lmo1134

(encoding putative transcriptional regulators); lmo0834, and lmo1188 (encoding proteins with unknown function); and lmo0333, lmo2470, and lmo2821 (encoding proteins similar to internalins). Indeed, the combined use of lmo2470 and lmo1116; or lmo0333 and lmo1116, or the use of lmo2821 alone is sufficient to enable identification of all potentially virulent *L. monocytogenes* strains under investigation. The scope of this invention also includes other genes identified by the methods described that could indicate virulent forms of *L. monocytogenes*. For example, the described techniques have been used to identify other genetic markers unique to *L. monocytogenes*, *L. innocua*, *L. grayi*, *L. ivanovii*, *L. seeligeri* and *L. welshimeri* (Table 5), that could be used for the development of species-specific PCR assays. These species-specific PCR assays have been tested against a panel of *Listeria* and other gram-positive and negative species.

TABLE 5

List of bacterial strains examined in PCR using Listeria species-specific primers

| Strain | Serovar | Source | lmo0733 (455 bp) | lin0464 (749 bp) | Lgr20-246 (420 bp) | Liv22-228 (467 bp) | Lse24-315 (371 bp) | Lwe7-571 (608 bp) |
|---|---|---|---|---|---|---|---|---|
| *L. monocytogenes* ATCC 19111 | 1 | Poultry | + | − | − | − | − | − |
| *L. monocytogenes* ATCC 19112 | 2 | Human | + | − | − | − | − | − |
| *L. monocytogenes* ATCC 19113 | 3 | Human | + | − | − | − | − | − |
| *L. monocytogenes* ATCC 19114 | 4a | Human | + | − | − | − | − | − |
| *L. monocytogenes* ATCC 19115 | 4b | Human | + | − | − | − | − | − |
| *L. monocytogenes* ATCC 19116 | 4c | Chicken | + | − | − | − | − | − |
| *L. monocytogenes* ATCC 19117 | 4d | Sheep | + | − | − | − | − | − |
| *L. monocytogenes* ATCC 19118 | 4e | Chicken | + | − | − | − | − | − |
| *L. monocytogenes* ATCC 15313 | 1 | Rabbit | + | − | − | − | − | − |
| *L. monocytogenes* EGD (NCTC7973) | ½a | Human | + | − | − | − | − | − |
| *L. monocytogenes* HCC7 | 1 | Catfish brain | + | − | − | − | − | − |
| *L. monocytogenes* HCC8 | 1 | Catfish brain | + | − | − | − | − | − |
| *L. monocytogenes* HCC12 | 4 | Catfish brain | + | − | − | − | − | − |
| *L. monocytogenes* HCC13 | 4 | Catfish kidney | + | − | − | − | − | − |
| *L. monocytogenes* HCC16 | 4 | Catfish brain | + | − | − | − | − | − |
| *L. monocytogenes* HCC17 | 4 | Catfish brain | + | − | − | − | − | − |
| *L. monocytogenes* HCC18 | 4 | Catfish spleen | + | − | − | − | − | − |
| *L. monocytogenes* HCC19 | 4 | Catfish spleen | + | − | − | − | − | − |
| *L. monocytogenes* HCC23 | 4 | Catfish brain | + | − | − | − | − | − |
| *L. monocytogenes* HCC24 | 4 | Catfish spleen | + | − | − | − | − | − |
| *L. monocytogenes* HCC25 | 4 | Catfish kidney | + | − | − | − | − | − |
| *L. monocytogenes* 168 | | Aborted calf fetus | + | − | − | − | − | − |
| *L. monocytogenes* 180 | | Human outbreak | + | − | − | − | − | − |
| *L. monocytogenes* 418 | | Freezer study | + | − | − | − | − | − |
| *L. monocytogenes* 742 | | Ground beef | + | − | − | − | − | − |
| *L. monocytogenes* 874 | | Cow brain | + | − | − | − | − | − |
| *L. monocytogenes* 1002 | | Pork sausage | + | − | − | − | − | − |
| *L. monocytogenes* 1084 | | Chicken | + | − | − | − | − | − |
| *L. monocytogenes* 1400 | | Jalisco outbreak | + | − | − | − | − | − |
| *L. innocua* ATCC 33090 | 6a | Cow brain | − | + | − | − | − | − |
| *L. innocua* 415 | | Turkey burger | − | + | − | − | − | − |
| *L. innocua* 416 | | Veal/beef patty | − | + | − | − | − | − |
| *L. innocua* 417 | | Beef steak | − | + | − | − | − | − |
| *L. innocua* 662 | | Raw milk | − | + | − | − | − | − |
| *L. innocua* 1419 | | Ground cheese | − | + | − | − | − | − |
| *L. innocua* 1425 | | Pecorino Romano | − | + | − | − | − | − |
| *L. innocua* 1720 | | Chicken | − | + | − | − | − | − |
| *L. innocua* 1944 | | Ground turkey | − | + | − | − | − | − |
| *L. grayi* ATCC 19120 | | Chinchilla faeces | − | − | + | − | − | − |
| *L. grayi* ATCC 25400 | | Corn leaves/stalks | − | − | + | − | − | − |
| *L. murrayi* ATCC 25401 | | Corn leaves/stalks | − | − | + | − | − | − |
| *L. ivanovii* ATCC 19119 | | Sheep | − | − | − | + | − | − |
| *L. ivanovii* 3325 | | Cheese | − | − | − | + | − | − |
| *L. seeligeri* ATCC 35967 | | Soil | − | − | − | − | + | − |
| *L. seeligeri* 3008 | | Soil | − | − | − | − | + | − |
| *L. seeligeri* 3321 | | Cheese | − | − | − | − | + | − |
| *L. welshimeri* ATCC 35897 | | Plant | − | − | − | − | − | + |
| *L. welshimeri* ATCC 43550 | ½b | Soil | − | − | − | − | − | + |
| *L. welshimeri* ATCC 43551 | 6a | Soil | − | − | − | − | − | + |
| *L. welshimeri* CCF4 | | Catfish brain | − | − | − | − | − | + |
| *L. welshimeri* 1471 | | Environment | − | − | − | − | − | + |
| *Aeromonas hydrophila* ATCC 35654 | | | − | − | − | − | − | − |
| *Clostridium perfringens* | | Clinical | − | − | − | − | − | − |
| *Enterococcus faecalis* ATCC 29212 | | | − | − | − | − | − | − |
| *Escherichia coli* ATCC 25922 | | | − | − | − | − | − | − |
| *Flavobacterium indolegenes* | | Clinical | − | − | − | − | − | − |
| *Klebsiella pneumoniae* ATCC 13883 | | | − | − | − | − | − | − |
| *Proteus vulgaris* ATCC 13315 | | | − | − | − | − | − | − |
| *Pseudomonas aeruginosa* ATCC 27853 | | | − | − | − | − | − | − |
| *Salmonella typhimurium* ATCC 14028 | | | − | − | − | − | − | − |
| *Serratia marcescens* ATCC 8100 | | | − | − | − | − | − | − |

TABLE 5-continued List of bacterial strains examined in PCR using Listeria species-specific primers

| Strain | Serovar | Source | lmo0733 (455 bp) | lin0464 (749 bp) | Lgr20-246 (420 bp) | Liv22-228 (467 bp) | Lse24-315 (371 bp) | Lwe7-571 (608 bp) |
|---|---|---|---|---|---|---|---|---|
| *Staphylococcus aureus* ATCC 25923 | | | – | – | – | – | – | – |
| *Streptococcus pneumoniae* | | Clinical | – | – | – | – | – | – |
| *Streptococcus pyogenes* ATCC 19615 | | | – | – | – | – | – | – |
| *Vibrio cholerae* | | Clinical | – | – | – | – | – | – |
| *Yersinia pseudotuberculosis* | | Clinical | – | – | – | – | – | – |

The present invention is also used to detect viable virulent strains of *L. monocytogenes*. The PCR assay utilized in the present invention is effective in amplifying the above listed gene sequences from chromosomal DNA, which is not effective in distinguishing live *L. monocytogenes* from dead *L. monocytogenes*. However, amplification of the above listed gene sequences from mRNA by reverse transcription-PCR (RT-PCR) would only detect the presence of live, viable *L. monocytogenes*.

Because transcriptional regulators are essential components in the regulation of RNA synthesis and gene expression within bacteria, and because internalins play vital roles in listerial internalization, they may be potentially useful targets for treatment and control purposes. Therefore, it is also within the scope of this invention to use *L. monocytogenes* virulence-specific genes (lmo0833, lmo1188, lmo0834, lmo1116, lmo2672, lmo1134, lmo0333, lmo2470, and lmo2821) or their derivatives in the inhibition of growth, reduction of pathogenicity, treatment and prevention of listeriosis caused by virulent strains of *Listeria monocytogenes.*

For example, one possible treatment strategy would involve using pharmaceutically active agent(s) that would inactivate or alter the function of one or more of the proteins encoded by the above listed genes, which would either kill the virulent *L. monocytogenes* or render it susceptible to the host immune system. One possible vaccine strategy would involve altering one or more of the above listed genes or promoter(s) for one or more of the above listed genes such that expression of the encoded protein(s) would be completely disrupted or altered. The said alteration or disruption of expression would render *L. monocytogenes* avirulent and effective as a live attenuated vaccine.

While the present invention has been described with reference to specific embodiments and exemplary bacteria species, it will be understood by those skilled in the art that a variety of changes may be made and the substitution of equivalents may be made without departing from the true spirit and scope of the present invention. Many modifications may be made to adapt a particular situation or a particular selected pathogen to the inclusive concept of the present invention. All such modifications or adaptations are intended to be within the scope of the claims appended hereto.

The complete disclosure of all references cited in this application are fully incorporated herein by reference.

REFERENCES

1. Ausubel, F. M., R. Brent, R. E. Kingston, D. D. Moore, J. G. Seidman, J. A. Smith, and K. Struhl (ed.). 1994. Current Protocols in Molecular Biology. John Wiley & Sons, New York, N.Y.

2. Aznar, R. & Alarcon, B. (2002). On the specificity of PCR detection of *Listeria monocytogenes* in food: a comparison of published primers. Syst Appl Microbiol 25, 109-119.

3. Bassler, H. A., Flood, S. J., Livak, K. J., Marmaro, J., Knorr, R. & Batt, C. A. (1995). Use of a fluorogenic probe in a PCR-based assay for the detection of *Listeria monocytogenes*. Appl Environ Microbiol 61, 3724-3728.

4. Blais, B. W., Turner, G., Sooknanan, R. & Malek, L. T. (1997). A nucleic acid sequence-based amplification system for detection of *Listeria monocytogenes* hlyA sequences. Appl Environ Microbiol 63, 310-313.

5. Bohne, J., H. Kestler, C. Uebele, Z. Sokolovic, and W. Goebel. 1996. Differential regulation of the virulence genes of *Listeria monocytogenes* by the transcriptional activator PrfA. Mol Microbiol 20:1189-98.

6. Bubert, A., Hein, I., Rauch, M l, Lehner, A., Yoon, B., Goebel, W., Wagner, M. 1999. Detection and differentiation of *Listeria* spp. by a single reaction based on multiplex PCR. Appl Environ Microbiol 65: 4688-92.

7. Bubert, A., Z. Sokolovic, S. K. Chun, L. Papathe-odorou, A. Simm, and W. Goebel. 1999. Differential expression of *Listeria monocytogenes* virulence genes in mammalian host cells. Mol Gen Genet 261:323-36.

8. Camilli, A., L. G. Tilney, and D. A. Portnoy. 1993. Dual roles of plcA in *Listeria monocytogenes* pathogenesis. Mol Microbiol 8:143-57.

9. Carpenter, S. L., and M. A. Harrison. 1989. Survival of *Listeria monocytogenes* on processed poultry. Journal of Food Science 54:556-557.

10. Domann, E., J. Wehland, M. Rohde, S. Pistor, M. Hartl, W. Goebel, M. Leimeister-Wachter, M. Wuenscher, and T. Chakraborty. 1992. A novel bacterial virulence gene in *Listeria monocytogenes* required for host cell microfilament interaction with homology to the proline-rich region of vinculin. Embo J 11:1981-90.

11. Donnelly, C. W., and G. J. Baigent. 1986. Method for flow cytometric detection of *Listeria monocytogenes* in milk. Appl Environ Microbiol 52:689-95.

12. Doyle, M. P., K. A. Glass, J. T. Beery, G. A. Garcia, D. J. Pollard, and R. D. Schultz. 1987. Survival of *Listeria monocytogenes* in milk during high-temperature, short-time pasteurization. Appl Environ Microbiol 53:1433-8.

13. Erdenlig, S., A. J. Ainsworth, and F. W. Austin. 1999. Production of monoclonal antibodies to *Listeria monocytogenes* and their application to determine the virulence of isolates from channel catfish. Appl Environ Microbiol 65:2827-32.

14. Erdenlig, S., A. J. Ainsworth, and F. W. Austin. 2000. Pathogenicity and production of virulence factors by *Listeria monocytogenes* isolates from channel catfish. J Food Prot 63:613-9.

15. Farber, J. M., A. Hughes, R. Holley, and B. Brown. 1989. Thermal resistance of *Listeria monocytogenes* in sausage meat. Acta Microbiol Hung 36:273-5.

16. Farber, J. M., and J. I. Speirs. 1987. Monoclonal antibodies directed against the flagellar antigens of *Listeria* species and their potential in EIA-based methods. Journal of Food Protection 50:479-484.

17. Franciosa, G., Tartaro, S., Wedell-Neergaard, C. & Aureli, P. (2001). Characterization of *Listeria monocytogenes* strains involved in invasive and noninvasive listeriosis outbreaks by PCR-based fingerprinting techniques. Appl Environ Microbiol 67, 1793-1799.

18. Freitag, N. E., and K. E. Jacobs. 1999. Examination of *Listeria monocytogenes* intracellular gene expression by using the green fluorescent protein of *Aequorea victoria*. Infect Immun 67:1844-52.

19. Gellin, B. G., and C. V. Broome. 1989. Listeriosis. Jama 261:1313-20.

20. Glaser, P., Frangeul, L., Buchrieser, C., Rusniok, C., Amend, A., Baquero, F., Berche, P., Bloecker, H., Brandt, P., Chakraborty, T., Charbit, A., Chetouani, F., Couve, E., de Daruvar, A., Dehoux, P., Domann, E., Dominguez-Bernal, G., Duchaud, E., Durant, L., Dussurget, O., Entian, K. D., Fsihi, H., Portillo, F. G., Garrido, P., Gautier, L., Goebel, W., Gomez-Lopez, N., Hain, T., Hauf, J., Jackson, D., Jones, L. M., Kaerst, U., Kreft, J., Kuhn, M., Kunst, F., Kurapkat, G., Madueno, E., Maitoumam, A., Vicente, J. M., Ng, E., Nedjari, H., Nordsiek, G., Novella, S., de Pablos, B., Perez-Diaz, J. C., Purcell, R., Remmel, B., Rose, M., Schlueter, T., Simoes, N., Tierrez, A., Vazquez-Boland, J. A., Voss, H., Wehland, J. & Cossart, P. (2001). Comparative genomics of *Listeria* species. Science 294, 849-852.

21. Glaser, P., L. Frangeul, C. Buchrieser, A. Amend, F. Baquero, P. Berche, H. Bloecker, P. Brandt, T. Chakraborty, A. Charbit, F. Chetouani, E. Couve, A. de Daruvar, P. Dehoux, E. Domann, G. Dominguez-Bernal, E. Duchaud, L. Durand, O. Dussurget, K.-D. Entian, H. Fsihi, F. Garcia-Del Portillo, P. Garrido, L. Gautier, W. Goebel, N. Gomez-Lopez, T. Hain, J. Hauf, D. Jackson, L.-M. Jones, U. Karst, J. Kreft, M. Kuhn, F. Kunst, G. Kurapkat, E. Madueno, A. Maitoumam, J. Mata Vicente, E. Ng, G. Nordsiek, S. Novella, B. de Pablos, J.-C. Perez-Diaz, B. Remmel, M. Rose, C. Rusniok, T. Schlueter, N. Simoes, A. Tierrez, J.-A. Vazquez-Boland, H. Voss, J. Wehland, and P. Cossart. 2001. From the pathogenic to the innocuous: comparison of the *Listeria monocytogenes* and the *Listeria innocua* genomes. GenBank Accession# NC_003210.

22. Graham, T. A., Golsteyn-Thomas, E. J., Thomas, J. E. & Gannon, V. P. (1997). Inter- and intraspecies comparison of the 16S-23S rRNA operon intergenic spacer regions of six *Listeria* spp. Int J Syst Bacteriol 47, 863-869.

23. Gray, M. L., and A. H. Killinger. 1966. *Listeria monocytogenes* and listeric infections. Bacteriol Rev 30:309-82.

24. Heisick, J. E., D. E. Wagner, M. L. Nierman, and J. T. Peeler. 1989. *Listeria* spp. found on fresh market produce. Appl Environ Microbiol 55:1925-7.

25. Hof, H., and J. Rocourt. 1992. Is any strain of *Listeria monocytogenes* detected in food a health risk? Int J Food Microbiol 16:173-82.

26. Klein, P. G. & Juneja, V. K. (1997). Sensitive detection of viable *Listeria monocytogenes* by reverse transcription-PCR. Appl Environ Microbiol 63, 4441-4448.

27. Kuhn, M., and W. Goebel. 1995. Molecular studies on the virulence of *Listeria monocytogenes*. Genet Eng (N Y) 17:31-51.

28. Lamont, R. J., R. Postlethwaite, and A. P. MacGowan. 1988. *Listeria monocytogenes* and its role in human infection. J Infect 17:7-28.

29. Lennon, D., Lewis, B., Mantell, C., Becroft, D., Dove, B., Farmer, K., Tonkin, S., Yeates, N., Stamp, R. & Mickleson, K. (1984). Epidemic perinatal listeriosis. Pediatr Infect Dis 3, 30-34.

30. Liu, D. 1994. Development of gene probes of *Dichelobacter nodosus* for differentiating strains causing virulent, intermediate or benign ovine footrot. Br Vet J 150:451-62.

31. Liu, D., and W. K. Yong. 1993. *Dichelobacter nodosus*: differentiation of virulent and benign strains by gene probe based dot blot hybridisation. Vet Microbiol 38:71-9.

32. Nishibori, T., Cooray, K., Xiong, H., Kawamura, I., Fujita, M. & Mitsuyama, M. (1995). Correlation between the presence of virulence-associated genes as determined by PCR and actual virulence to mice in various strains of *Listeria* spp. Microbiol Immunol 39, 343-349.

33. Norton, D. M. & Batt, C. A. (1999). Detection of viable *Listeria monocytogenes* with a 5' nuclease PCR assay. Appl Environ Microbiol 65, 2122-2127.

34. Norton, D. M., Scarlett, J. M., Horton, K., Sue, D., Thimothe, J., Boor, K. J. & Wiedmann, M. (2001). Characterization and pathogenic potential of *Listeria monocytogenes* isolates from the smoked fish industry. Appl Environ Microbiol 67, 646-653.

35. Pine, L., Kathariou, S., Quinn, F., George, V., Wenger, J. D. & Weaver, R. E. (1991). Cytopathogenic effects in enterocytelike Caco-2 cells differentiate virulent from avirulent *Listeria* strains. J Clin Microbiol 29, 990-996.

36. Portnoy, D. A., Jacks, P. S. & Hinrichs, D. J. (1988). Role of hemolysin for the intracellular growth of *Listeria monocytogenes*. J Exp Med 167, 1459-1471.

37. Portnoy, D. A., T. Chakraborty, W. Goebel, and P. Cossart. 1992. Molecular determinants of *Listeria monocytogenes* pathogenesis. Infect Immun 60:1263-7.

38. Poyart, C., E. Abachin, I. Razafimanantsoa, and P. Berche. 1993. The zinc metalloprotease of *Listeria monocytogenes* is required for maturation of phosphatidylcholine phospholipase C: direct evidence obtained by gene complementation. Infect Immun 61:1576-80.

39. Roche, S. M., Velge, P., Bottreau, E., Durier, C., Marquet-van der Mee, N. & Pardon, P. (2001). Assessment of the virulence of *Listeria monocytogenes*: agreement between a plaque-forming assay with HT-29 cells and infection of immunocompetent mice. Int J Food Microbiol 68, 33-44.

40. Rodler, M., and W. Korbler. 1989. Examination of *Listeria monocytogenes* in milk products. Acta Microbiol Hung 36:259-61.

41. Sallen B, Rajoharison A, Desvarenne S, Quinn F, Mabilat C., 1996. Comparative analysis of 16S and 23S rRNA sequences of *Listeria* species. Int J Syst Bacteriol. 46:669-74.

42. Schuchat, A., B. Swaminathan, and C. V. Broome. 1991. Epidemiology of human listeriosis. Clin Microbiol Rev 4:169-83.

43. Smith, G. A., H. Marquis, S. Jones, N. C. Johnston, D. A. Portnoy, and H. Goldfine. 1995. The two distinct phospholipases C of *Listeria monocytogenes* have overlapping roles in escape from a vacuole and cell-to-cell spread. Infect Immun 63:4231-7.

44. Vazquez-Boland, J. A., C. Kocks, S. Dramsi, H. Ohayon, C. Geoffroy, J. Mengaud, and P. Cossart. 1992. Nucleotide sequence of the lecithinase operon of *Listeria monocytogenes* and possible role of lecithinase in cell-to-cell spread. Infect Immun 60:219-30.

45. Vazquez-Boland, J. A., Kuhn, M., Berche, P., Chakraborty, T., Dominguez-Bernal, G., Goebel, W., Gonzalez-Zorn, B., Wehland, J. & Kreft, J. (2001). *Listeria* pathogenesis and molecular virulence determinants. Clin Microbiol Rev 14, 584-640.

46. Wiedmann, M., Bruce, J. L., Keating, C., Johnson, A. E., McDonough, P. L. & Batt, C. A. (1997). Ribotypes and virulence gene polymorphisms suggest three distinct *Listeria monocytogenes* lineages with differences in pathogenic potential. Infect Immun 65, 2707-2716.

47. Winters, D. K., Maloney, T. P. & Johnson, M. G. (1999). Rapid detection of *Listeria monocytogenes* by a PCR assay specific for an aminopeptidase. Mol Cell Probes 13, 127-131.

What is claimed is:

1. An isolated nucleic acid, wherein said nucleic acid consists of the sequence as set forth in SEQ ID NO:9 or is complementary to SEQ ID NO:9.

2. The isolated nucleic acid of claim 1, wherein said nucleic acid encodes a protein having virulent biological activity.

3. The isolated nucleic acid of claim 1, wherein a vector comprises said sequence.

4. The isolated nucleic acid of claim 3, wherein a host cell comprises said vector.

5. The isolated nucleic acid of claim 1, wherein said sequence comprises a contiguous reading frame from about residue 887 to 1500 of SEQ ID NO:9.

6. The isolated nucleic acid of claim 5, wherein said complement specifically hybridizes to said contiguous reading frame in an *L. monocytogenes* strain selected from the group consisting of *L. monocytogenes* ATCC 19111 serovar 1, *L. monocytogenes* ATCC 19112 serovar 2, *L. monocytogenes* ATCC 19113 serovar 3, *L. monocytogenes* ATCC 19115 serovar 4b, *L. monocytogenes* ATCC 19116 serovar 4c, *L. monocytogenes* ATCC 19116 serovar 4d, *L. monocytogenes* ATCC 19118 serovar 4e, *L. monocytogenes* ATCC 15313 serovar 1, *L. monocytogenes* EDG (NCTC 7973) serovar 1/2a, *L. monocytogenes* HCC7 serovar 1, *L. monocytogenes* HCC8 serovar 1, *L. monocytogenes* 168, *L. monocytogenes* 180, *L. monocytogenes* 418, *L. monocytogenes* 742, *L. monocytogenes* 874, *L. monocytogenes* 1002, *L. monocytogenes* 1084, and *L. monocytogenes* 1400.

7. The isolated nucleic acid of claim 6, wherein said contiguous reading frame encodes an amino acid sequence 203 residues in length.

8. The isolated nucleic acid of claim 1, wherein said sequence hybridizes to residues 479-1500 of SEQ ID NO:9.

9. The isolated nucleic acid of claim 8, wherein said hybridizing sequence is SEQ ID NO:27.

10. The isolated nucleic acid of claim 1, wherein said sequence hybridizes to the complement of residues 887-900 of SEQ ID NO:9.

11. The isolated nucleic acid of claim 10, wherein said hybridizing sequence is SEQ ID NO:26.

12. An isolated nucleic acid complex comprising:

a) at least two primers, wherein one of said at least two primers comprises the sequence as set forth in SEQ ID NO:26 or SEQ ID NO:27; and b) a nucleic acid comprising the sequence as set forth in SEQ ID NO:9, wherein said nucleic acid is isolated from an *L. monocytogenes* strain.

13. The isolated nucleic acid complex of claim 12, wherein said *L. monocytogenes* strain is selected from the group consisting of *L. monocylogenes* ATCC 19111 serovar 1, *L. monocytogenes* ATCC 19112 serovar 2, *L. monocytogenes* ATCC 19113 serovar 3, *L. monocytogenes* ATCC 19115 serovar 4b, *L. monocytogenes* ATCC 19116 serovar 4c, *L. monocytogenes* ATCC 19116 serovar 4d, *L. monocytogenes* ATCC 19118 serovar 4e, *L. monocytogenes* ATCC 15313 serovar 1, *L. monocytogenes* EDG (NCTC 7973) serovar 1/2a, *L. monocytogenes* HCC7 serovar 1, *L. monocytogenes* HCC8 serovar 1, *L. monocytogenes* 168, *L. monocytogenes* 180, *L. monocytogenes* 418, *L. monocytogenes* 742, *L. monocytogenes* 874, *L. monocytogenes* 1002, *L. monocytogenes* 1084, and *L. monocytogenes* 1400.

* * * * *